(12) United States Patent
Gray et al.

(10) Patent No.: US 7,762,793 B2
(45) Date of Patent: Jul. 27, 2010

(54) INFUSION DEVICE AND DRIVING MECHANISM AND PROCESS FOR SAME WITH ACTUATOR FOR MULTIPLE INFUSION USES

(75) Inventors: John Gray, Los Angeles, CA (US);
Robert W. Bosley, Cerritos, CA (US);
Eric Lorenzen, Granada Hills, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 1014 days.

(21) Appl. No.: 11/218,223

(22) Filed: Aug. 31, 2005

(65) Prior Publication Data

US 2006/0056998 A1    Mar. 16, 2006

Related U.S. Application Data

(60) Continuation of application No. 10/925,065, filed on Aug. 23, 2004, now Pat. No. 6,945,760, which is a division of application No. 10/331,132, filed on Dec. 26, 2002, now Pat. No. 6,932,584.

(51) Int. Cl.
*F04B 35/04* (2006.01)
*H02K 41/00* (2006.01)
*H02K 33/00* (2006.01)
*A61M 1/00* (2006.01)

(52) U.S. Cl. ............................ 417/417; 310/14; 310/23; 604/152

(58) Field of Classification Search ................. 417/417; 310/14, 15, 17, 23, 24, 30, 36; 604/131, 604/141, 15, 890.122
See application file for complete search history.

(56) References Cited

U.S. PATENT DOCUMENTS

| | | | |
|---|---|---|---|
| 3,302,582 A * | 2/1967 | Kofink | ........................ 417/417 |
| 4,193,397 A | 3/1980 | Tucker et al. | |
| 4,245,789 A | 1/1981 | Gray | |
| 4,373,527 A | 2/1983 | Fischell | |
| 4,437,815 A | 3/1984 | McMullen | |
| 4,468,221 A | 8/1984 | Mayfield | |

(Continued)

OTHER PUBLICATIONS

PCT International Search Report as issued in International Application No. PCT/US02/28081, Mailing date Jun. 18, 2003.

(Continued)

*Primary Examiner*—Charles G Freay
(74) *Attorney, Agent, or Firm*—Scott A. Marks, Esq.; Foley & Lardner, LLP

(57) ABSTRACT

A drive mechanism for delivery of infusion medium a coil capable of being electrically activated to provide an electromagnetic field. The coil surrounds a piston channel extending in an axial direction. An armature is located adjacent the coil, on one side of the axial channel. The armature is moveable toward a forward position, in response to the electromagnetic field produced by activation of the coil. A piston is located within the piston channel and is moveable axially within the channel to a forward position, in response to movement of the armature to its forward position. The armature and piston are moved toward a retracted position, when the coil is not energized. The armature may be configured with a reduced diameter by including a coil cup for supporting the coil including a shelf portion defining at least a portion of a pole surface of the coil cup.

42 Claims, 15 Drawing Sheets

U.S. PATENT DOCUMENTS

| | | | | |
|---|---|---|---|---|
| 4,487,603 A | * | 12/1984 | Harris | 604/152 |
| 4,557,726 A | * | 12/1985 | Reinicke | 604/67 |
| 4,568,250 A | | 2/1986 | Falk et al. | |
| 4,569,641 A | | 2/1986 | Falk et al. | |
| 4,573,994 A | | 3/1986 | Fischell et al. | |
| 4,576,556 A | | 3/1986 | Thompson | |
| 4,594,058 A | | 6/1986 | Fischell | |
| 4,636,150 A | | 1/1987 | Falk et al. | |
| 4,684,368 A | * | 8/1987 | Kenyon | 604/152 |
| 4,692,147 A | | 9/1987 | Duggan | |
| 4,697,622 A | | 10/1987 | Swift et al. | |
| 4,714,234 A | | 12/1987 | Falk et al. | |
| 4,715,852 A | * | 12/1987 | Reinicke et al. | 604/131 |
| 4,808,089 A | | 2/1989 | Buchholtz | |
| 4,883,467 A | * | 11/1989 | Franetzki et al. | 604/152 |
| 4,985,015 A | | 1/1991 | Obermann et al. | |
| 5,167,633 A | | 12/1992 | Mann et al. | |
| 5,176,644 A | | 1/1993 | Srisathapat et al. | |
| 5,315,278 A | * | 5/1994 | Demere et al. | 335/282 |
| 5,318,521 A | | 6/1994 | Slettenmark | |
| 4,373,527 A | | 6/1995 | Fischell | |
| 5,514,103 A | | 5/1996 | Srisathpat et al. | |
| 5,527,307 A | | 6/1996 | Srisathpat et al. | |
| 5,797,733 A | | 8/1998 | Falk et al. | |
| 5,975,437 A | | 11/1999 | Streicher et al. | |
| 6,193,477 B1 | * | 2/2001 | Falk et al. | 417/415 |
| 6,227,818 B1 | | 5/2001 | Falk et al. | |
| 6,595,756 B2 | * | 7/2003 | Gray et al. | 417/44.1 |
| 6,652,252 B2 | * | 11/2003 | Zabar | 417/417 |
| 6,770,067 B2 | * | 8/2004 | Lorenzen et al. | 604/891.1 |
| 6,932,584 B2 | * | 8/2005 | Gray et al. | 417/417 |

OTHER PUBLICATIONS

International Search Report dated Jun. 7, 2005 from related PCT application No. PCT/US2003/038352.

Notice of Allowance dated May 10, 2005 from related U.S. Appl. No. 10/925,065.

Office Action dated Apr. 19, 2005 form related U.S. Appl. No. 10/925,065.

Office Action on Mar. 3, 2004 form related U.S. Appl. No. 10/331,132.

Notice of Allowance dated Apr. 20, 2005 from related U.S. Appl. No. 10/331,132.

* cited by examiner

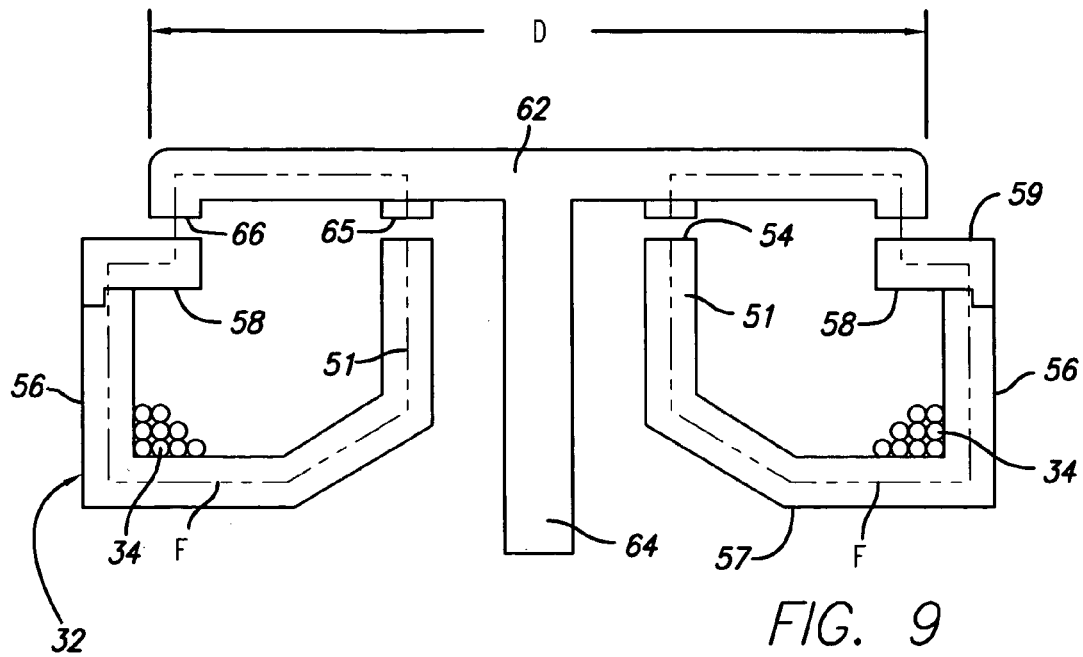
FIG. 9
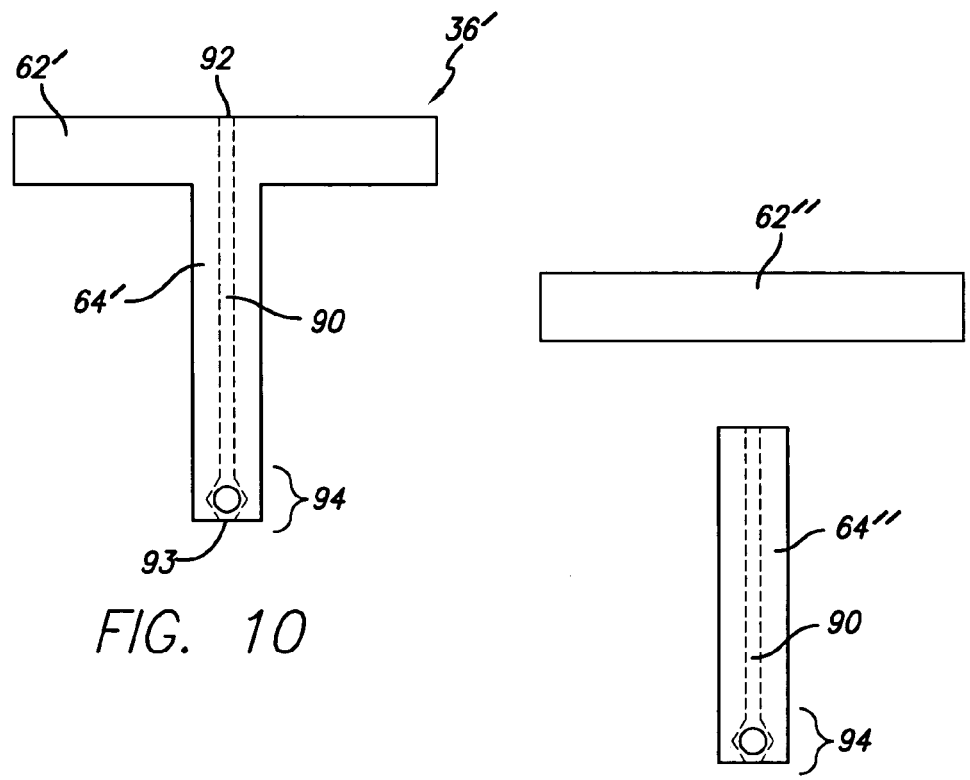
FIG. 10
FIG. 11

INFUSION DEVICE AND DRIVING MECHANISM AND PROCESS FOR SAME WITH ACTUATOR FOR MULTIPLE INFUSION USES

CROSS-REFERENCE TO RELATED PATENT APPLICATIONS

This application is a Continuation of U.S. application Ser. No. 10/925,065, filed Aug. 23, 2004, now U.S. Pat. No. 6,945,760 incorporated herein by reference in its entirety, which is a Division of U.S. application Ser. No. 10/331,132, filed Dec. 26, 2002, now U.S. Pat. No. 6,932,584 incorporated herein by reference in its entirety.

FIELD OF THE INVENTION

The present invention relates generally to infusion devices, systems and processes and, in particular embodiments to infusion devices, systems and processes employing a drive mechanism configuration having an actuator configured for improved efficient operation with a variety of types of infusion media. Further embodiments of the invention relate to drive mechanisms for such infusion devices and systems, and processes of making and using such drive mechanisms.

BACKGROUND

Infusion devices are typically used to deliver infusion media, such as medication, to patients. An implantable infusion device is designed to be implanted in a patient's body, to administer an infusion medium to the patient at a regulated dosage. An external infusion device is designed to be located outside of the patient's body and connected to the patient by a suitable catheter, tubing or the like, to administer an infusion medium into the patient's body.

Both implantable and external infusion devices may include one or more pump drive mechanisms for creating pumping forces to cause or help delivery of infusion media to the patients. Various types of pump drive mechanisms with electromagnetic drive devices have been developed for such infusion devices. Such pump drive devices typically include an electromagnetic actuator having an armature portion made of a magnetically conductive material. The armature interacts, electromagnetically, with an electrical coil housed in a coil cup made of magnetically conductive material. Such drive mechanisms include, for example, the drive mechanisms described in U.S. patent application entitled "Infusion Device and Driving Mechanism For Same," Ser. No. 10/033,722, filed Dec. 27, 2001, by the owner of the present invention. Other pump drive mechanisms having electromagnetic armature-coil assemblies include, for example, those described in U.S. Pat. No. 4,594,058 to Fischell; U.S. Pat. No. 4,684,368 to Kenyon; U.S. Pat. No. 4,569,641 to Falk et al.; U.S. Pat. No. 4,568,250 to Falk, et al.; U.S. Pat. No. 4,636,150 to Falk, et al.; and U.S. Pat. No. 4,714,234 to Falk et al.

Pump drive mechanisms for infusion devices (including those referenced above) may include components, such as actuators, that come into direct contact with the infusion medium during normal operation. In such infusion devices, the chemical interaction of the infusion medium with materials used for such components may have an adverse effect on the patient to which the infusion medium is administered. The risk of such an adverse effect may be greater for implantable infusion devices, where components of an infusion pump may remain in contact with infusion medium over a prolonged period of time inside of an implanted device. For example, contact with the armature may cause leaching or other interactions of materials between the infusion medium and the armature. Such interactions may adversely alter the medical effect of the infusion medium on the patient. Prolonged contact may cause other detrimental effects, such as corrosion of the armature.

Pump drive mechanisms may be manufactured for use with a particular, known infusion medium, in which case, the effect (and prolonged effect) of direct contact of that particular infusion medium on components of the pump drive mechanism may be studied in advance. With such studies, the materials and components of the infusion pump may be selected and designed to be in contact with the infusion medium, yet, have a suitably benign effect on the patient. However, if the particular type of infusion medium is not known at the time of manufacture of the pump mechanism, for example, in the case in which a pump mechanism is being manufactured for multiple possible infusion uses, the ability to study effects on all possible infusion media may not be practical or possible. Accordingly, there is a demand in the industry for a pump mechanism and process that is suitable for multiple possible infusion uses.

In some contexts of use, the infusion device must be operable for an extended period with a limited power supply. For example, battery powered infusion devices may be implanted in or otherwise connected to patients, to deliver medication at controlled intervals over a prolonged period of time. A battery replacement in an implanted device may require surgery on the patient to remove and re-implant the device. Accordingly, there is a demand in the industry for infusion devices which make efficient use of power supplies and, thus, require fewer or no power supply replacements.

Because implantable infusion devices are designed to be implanted in the patient's body, the dimensions of such devices can have an impact on the determination of the location in the body at which a device may be implanted, the level of comfort of the implant patient and the external appearance of the implant site. Typically, a device with relatively small dimensions and, in particular, a relatively small thickness form factor, will provide greater flexibility in the choice of location in the patient's body to place the implant and will minimize patient discomfort and minimize noticeable protrusions at the implant site. Accordingly, there is a demand in the industry for minimizing the overall dimensions, and, in particular, the thickness dimension of implantable infusion device.

SUMMARY OF THE DISCLOSURE

Accordingly, embodiments of the present invention relate to infusion devices and drive mechanisms for infusion devices which address one or more of the above-mentioned industry demands.

Embodiments of the invention relate to such devices and drive mechanisms configured for use with any one of multiple different infusion media.

Further embodiments relate to such devices and drive mechanisms configured and operated to make highly efficient use of electrical power to prolong operational life.

Further embodiments of the invention relate to such devices and drive mechanisms configured for implantation in a patient's body and, thus, configured to have a relatively small thickness dimension, for example, to minimize trauma to the implant recipient (referred to herein as the patient). However, aspects of the invention may apply to external infusion devices and drive mechanisms for such external devices and, thus, other embodiments of the invention relate to such external infusion devices and drive mechanisms.

An implantable infusion device according to an embodiment of the invention includes a housing made from a biocompatible and infusion medium compatible material. The infusion device housing contains a reservoir for holding a volume of infusion medium, such as, but not limited to, a medication to be administered to the patient. The infusion device housing has an outlet through which the infusion medium may be expelled.

The infusion device further includes a drive mechanism having an inlet coupled in fluid flow communication with the reservoir and an outlet coupled in fluid flow communication with the infusion device housing outlet. The drive mechanism employs electromagnetic and mechanical forces to move an actuator piston between retracted and forward positions or states, to cause infusion medium to be drawn from the reservoir, through an inlet and forced out of an outlet.

A drive mechanism, according to one embodiment, comprises an assembly of components which may be manufactured and assembled in a relatively cost efficient manner. The components include a housing containing a coil disposed within a coil cup and a piston channel surrounded by the coil. The components also include an actuator having a piston extending through the piston channel and an armature disposed at one end of the piston channel. A piston chamber, outlet chamber and outlet valve are located at the other end of the piston channel.

According to embodiments of the present invention, the coil cup may be composed of a magnetizable material and may include a generally annular outer wall, the outer wall having a generally annular shelf portion extending from the outer wall towards the inner wall. The shelf portion has an end defining an outer pole surface of the coil cup. In one embodiment of the present invention, the inner wall of the coil cup includes a generally annular shelf portion extending from the inner wall towards the outer wall. The shelf portion has an end defining at least a portion of an inner pole surface of the coil cup. The coil cup includes a generally annular interior between the outer and inner walls. The annular interior contains a coil.

When the coil is in a quiescent state, the armature and piston are urged toward a retracted position by mechanical or magnetic forces. When the coil is energized, the armature and piston move to a forward stroke position. The movement of the piston from a retracted position to a forward position creates pressure differentials within the drive mechanism to drive medium out the outlet. Mechanical force may return the piston to the retracted position. The movement of the piston from a forward position to a retracted position creates pressure differentials to draw medium into the drive mechanism inlet and into the piston chamber.

Various types of electromagnetic actuator type drive mechanisms for infusion devices have been configured with actuators having an armature portion made of a magnetically conductive material. The armature interacts, electromagnetically, with an electrical coil housed in a coil cup made of magnetically conductive material. An example of a pump drive mechanism suitable for an implantable infusion device is described in U.S. patent application entitled "Infusion Device and Driving Mechanism For Same," Ser. No. 10/033,722, filed Dec. 27, 2001, by the owner of the present invention. Certain embodiments of the present invention include a pump drive mechanism as described in U.S. patent application Ser. No. 10/033,722, but with differences relating to the actuator and/or coil cup configuration and operation as described herein. Other embodiments may employ other suitable pump drive mechanisms having actuator and/or coil cup aspects as described herein.

As described in further detail below, armature portions of actuators employed in embodiments of the present invention may be configured with a reduced diameter, for example, to reduce fluidic resistance to actuator movement. Alternatively, or in addition, further embodiments of the present invention employ an armature structure that is free of apertures (or employs a reduced number of apertures as compared to actuators described in U.S. patent application Ser. No. 10/033,722) and, thus, may be provided with a protective layer or coating in a simplified manufacturing process.

Other embodiments may employ an armature that may be manufactured from any suitable material, including materials having a low magnetic permeability. According to these embodiments, the armature portion of the actuator may be formed with a cavity into which a material having a relatively high magnetic permeability may be placed. These materials may be, for example, ferrous materials.

Alternatively, or in addition, actuators according to further embodiments of the invention employ a piston portion that has a central channel and valve structure for increasing the flow rate of infusion medium into a pumping chamber and inhibiting backflow of infusion medium from the pumping chamber. In yet further embodiments, the diameter of the piston portion may be reduced and/or the diameter of the piston channel in which the piston moves may be increased, to increase the flow rate of infusion medium into the pumping chamber. By accommodating an increased flow rate, the drive mechanisms may be operable with a greater variety of infusion media.

Embodiments of the invention may employ a coaxial arrangement of the piston, the piston channel and the coil, to provide significant advantages with respect to providing a relatively thin form factor and efficient power usage. A number of features described herein and in U.S. patent application Ser. No. 10/033,722 can each provide or be combined to contribute to a reduction in the thickness form factor of the drive mechanism. For example, a coaxial arrangement of components can be implemented with a smaller thickness form factor than alternative arrangements in which components are arranged in series with each other in the thickness dimension. Embodiments may include an inlet volume or chamber on one side of the coil and an outlet chamber on the opposite side of the coil, with a flow passage through the piston channel, such that the coil and flow channel share a common portion of the thickness dimension. The armature may be located within the inlet volume and, thus, share a common portion of the thickness dimension with the inlet volume. The outlet chamber may be centrally located within the same housing that has the coil cup and formed in relatively close proximity to the coil cup in the thickness dimension of the housing.

In addition, a number of features described herein and in U.S. patent application Ser. No. 10/033,722 can provide, or be combined to contribute to, the efficient use of power to, prolong the operational life of the drive mechanism.

These and other aspects and advantages of the invention will be apparent to one of skill in the art from the accompanying detailed description and drawings.

BRIEF DESCRIPTION OF THE DRAWINGS

Referring now to the drawings in which like reference numbers represent corresponding parts throughout:

FIG. 9 is a simplified cross-section diagram, showing an arrangement of an actuator member and coil cup member for the drive mechanism in FIG. 3A.

FIG. 10 is a simplified cross-section diagram, showing another embodiment of an actuator comprising an armature and a piston for a drive mechanism of the type shown in FIGS. 3A-D and 4A-D.

FIG. 11 is a simplified cross-section diagram, showing another embodiment of an actuator comprising a 2-piece structure having an armature and a piston, for a pump drive mechanism.

DETAILED DESCRIPTION OF PREFERRED EMBODIMENTS

The following detailed description is of the best presently contemplated mode of implementing the invention. This description is not to be taken in a limiting sense, but is made merely for the purpose of illustrating the general principles of embodiments of the invention. The scope of the invention is best defined by the appended claims.

As discussed above, the present invention relates generally to infusion devices having drive mechanisms and also to drive mechanism configurations for infusion of a medium into a patient or other environment. Embodiments of the invention relate to such devices and drive mechanisms configured for use with any one of multiple different infusion media.

Embodiments of the invention relate to such devices and drive mechanisms configured for implantation in a patient's body. Embodiments described herein allow the drive mechanism for such infusion device to have a relatively small thickness dimension, for example, to minimize trauma to the implant recipient (referred to herein as the patient). Further preferred embodiments relate to such devices and drive mechanisms configured and operated to make highly efficient use of electrical power to prolong operational life in an implant environment. However, because aspects of the invention may be applied to external infusion devices as well, yet further embodiments of the invention relate to such external infusion devices and drive mechanisms for such external devices.

Figure 1:
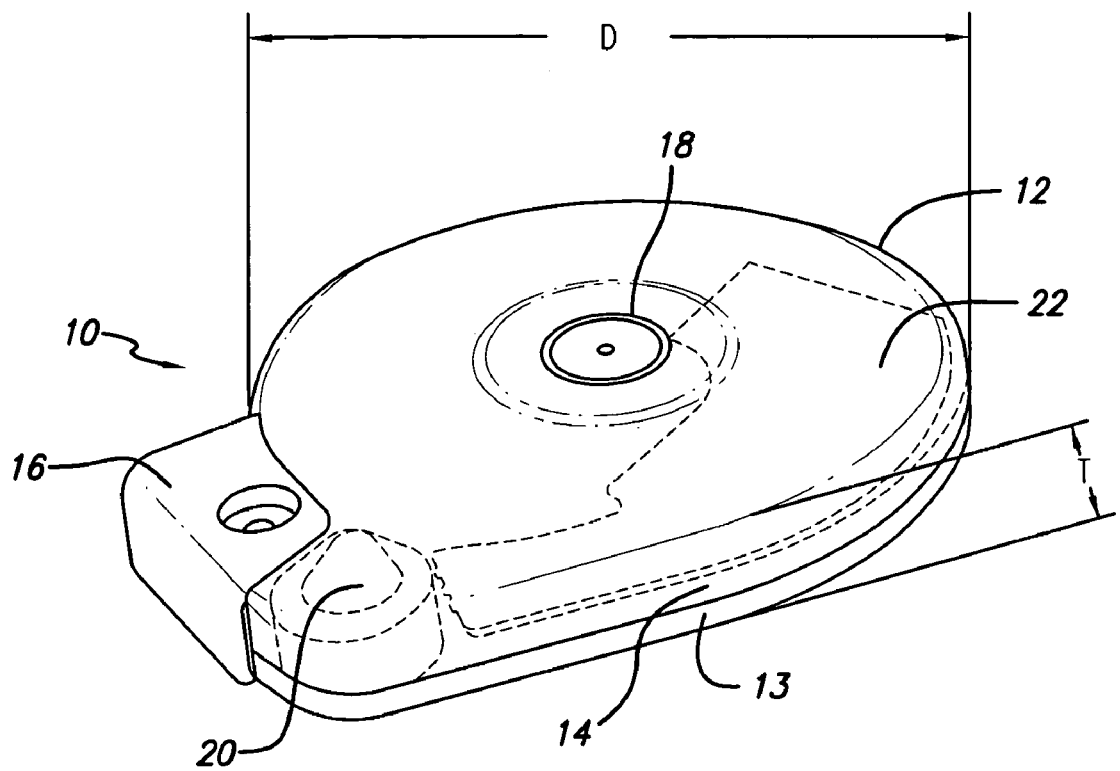
FIG. 1 is a perspective view of an implantable infusion device according to an embodiment of the invention.

FIG. 1 shows an implantable infusion device 10 according to an embodiment of the invention. The illustrated device 10 is configured to be surgically implanted into a patient, for example, in the abdominal region, between the skin and the abdominal wall. A catheter connected to the pump may deliver infusion medium to the patient, for example, by feeding infusion medium to a particular location in the venous system, in the spinal column, in the peritoneal cavity, or in another suitable location of the patient.

Preferred embodiments of the device 10 are configured in accordance with one or more aspects of the invention for enhancing operability with multiple types of infusion media, enhancing power usage efficiency and simplifying implantation. As noted above, further embodiments of the invention may be implemented as external infusion devices, which connect to patients through suitable catheter devices or the like. Yet further embodiments of the invention may be used in other contexts, for delivery of a medium into other suitable environments. Therefore, for purposes of simplifying the present disclosure, the term "patient" is used herein to refer to the entity or environment in which an implantable device is implanted or to which an external device is connected, whether or not the implant or connection is carried out for medical purposes. Also, the term "infusion medium" is used herein to refer to any suitable medium delivered by the drive device.

The device 10 in FIG. 1 includes a generally disc-shaped housing 12. While a generally circular disc-shaped embodiment is illustrated in FIG. 1, further embodiments of the invention may employ housings of other shapes, including, but not limited to, oval, oblong, rectangular, or other curved or polygonal shapes. The housing 12 has a diameter dimension D, defining the diameter of the disc shape, and a maximum thickness dimension T, defining the maximum thickness of the device.

In implantable device embodiments, the housing 12 preferably is made of a biocompatible material, is hermetically sealed from the external environment and has a relatively small or minimized thickness dimension T, to reduce or minimize patient trauma during implant surgery and after implantation. For example, the housing 12 may be made from titanium, titanium alloy, stainless steel or other biocompatible materials and may be configured to provide a hermetically sealed environment for some or all of the components within the interior of the housing.

The housing 12 includes a reservoir housing portion 13 containing a reservoir for holding a volume of infusion medium, such as, but not limited to, a liquid medication to be administered to the patient. The housing 12 includes a further housing portion 14, located above the reservoir housing portion 13 in the orientation shown in FIG. 1, for containing a drive mechanism 20, a power source and control electronics 22 described below.

Representative examples of reservoir housing portions and reservoirs which may be employed in embodiments of the invention are described in co-pending U.S. patent application Ser. No. 10/033,377, titled "Implantable Infusion Device And Reservoir For Same," which is incorporated herein by reference. However, further embodiments may employ other suitable reservoir configurations, including, but not limited to, those described in U.S. Pat. No. 5,514,103 and U.S. Pat. No. 5,176,644, each to Srisathapat et al, U.S. Pat. No. 5,167,633 to Mann et al., U.S. Pat. No. 4,697,622 to Swift and U.S. Pat. No. 4,573,994 to Fischell et al.

The housing 12 also has an outlet 16 through which the infusion medium may be expelled. When the device 10 is implanted in a patient or connected externally to a patient, a catheter may be connected to the outlet 16, to deliver infusion medium expelled from the outlet 16 into the patient's blood stream or to a selected location in the patient's body. The infusion device 10 may also include an inlet structure 18 which provides a closeable and sealable fluid flow path to the reservoir in the reservoir portion 13 of the housing. In an example embodiment, the inlet structure provides a port for receiving a needle through which fluid may be transferred to the infusion device, for example, to fill or re-fill the reservoir of the device. The inlet structure may be configured to re-seal after a fill or re-fill operation, to allow multiple re-fill and re-seal operations.

One example of an inlet structure is described in co-pending U.S. patent application Ser. No. 10/034,628, titled "Infusion Device And Inlet Structure For Same," which is incorporated herein by reference. However, further embodiments may employ other suitable inlet structures, including, but not limited to, those described in U.S. Pat. No. 5,514,103 and U.S. Pat. No. 5,176,644, each to Srisathapat et al, U.S. Pat. No. 5,167,633 to Mann et al., U.S. Pat. No. 4,697,622 to Swift and U.S. Pat. No. 4,573,994 to Fischell et al.

As described above, preferred embodiments of the device 10 are configured in accordance with one or more aspects of the invention for enhancing operability with multiple types of infusion media. In such embodiments, any one of various types of infusion media having different compositions, concentrations and/or chemical characteristics may be contained, filled or re-filled into the reservoir for a given infusion treatment program. Thus, in such embodiments, the components of the reservoir, inlet and outlet structures that come into contact with the infusion medium may be made with (or coated with) a suitable material that will minimize the risk of having an adverse reaction with a any of the multiple types of infusion media that may be contained in the reservoir. Suitable materials may include, but are not limited to, titanium, titanium alloy, stainless steel or the like.

The infusion device 10 includes a drive mechanism 20, such as a pump, and an electronic control system 22 located in the housing portion 14. The drive mechanism 20 is connected between the reservoir and the outlet 16. The electronic control system 22 includes a power source, such as a battery, and control electronics for controlling the drive mechanism 20 to deliver infusion medium from the reservoir, to the patient in a selected manner. The drive mechanism may be controlled to deliver infusion medium in any suitable manner, for example, according to a programmed dispensing rate or schedule, according to an actuation signal from a sensor, timer, manual actuator or other suitable source, or combinations thereof.

The programmed dispensing rate or schedule may be different for different types of infusion media. Thus, the control system 22 may include programmable electronics which allow programming of dispensing functions, including rate, schedule, dispensing time, dispensing period, sensor activities that trigger dispensing and the like, depending upon the type of infusion medium contained in the reservoir. Such programming may be accomplished prior to implantation. In other embodiments, programming may be accomplished by a wireless communication link, after implantation. Systems for wireless communication between control electronics of an implanted infusion device and an external programming device are described in U.S. patent application Ser. No. 10/033,530, titled "Safety Limits for Closed-Loop Infusion Pump Control", filed Dec. 26, 2001, which is owned by the owner of the present invention.

An example of a pump drive mechanism suitable for an implantable infusion device is described in U.S. patent application entitled "Infusion Device and Driving Mechanism For Same," Ser. No. 10/033,724, filed Dec. 27, 2001, by the owner of the present invention and incorporated herein by reference. Certain embodiments of the present invention include a pump drive mechanism 20 similar to that described in U.S. patent application Ser. No. 10/033,722, but with differences relating to the actuator and/or coil cup configuration and operation as described herein. Other embodiments may employ other suitable pump drive mechanisms having actuator and/or coil cup aspects as described herein.

The pump drive mechanism described in U.S. patent application Ser. No. 10/033,724 employs an actuator having an armature portion that is formed with a plurality of apertures and radial rib sections. The apertures allow the armature portion to move in a volume of fluidic infusion media, with reduced fluidic resistance. This is accomplished, by allowing infusion media to pass through the apertures as the armature portion moves back and forth between forward and retracted positions. The radial ribs provide radial paths for electromagnetic flux between the pole surfaces of the armature. However, an armature structure that has a plurality of apertures and radial rib portions may be difficult to layer with a protective material or coating. It can be difficult to layer or apply coatings to all exposed surfaces formed by the apertures and ribs.

Accordingly, embodiments of the present invention employ an armature structure that is free of apertures (or employs a reduced number of apertures as compared to actuators described in U.S. patent application Ser. No. 10/033,722) and, thus, may be readily provided with a protective layer or coating in a simplified manufacturing process. Such armature portions may be configured with a reduced diameter, for example, to reduce fluidic resistance to actuator movement. Further embodiments of the invention employ an armature structure with apertures (as described in U.S. patent application Ser. No. 10/033,722), but with a reduced diameter, for example, to reduce fluidic resistance to motion and improve power usage efficiency.

Alternatively, or in addition, actuators according to further embodiments of the invention employ a piston portion that has a central channel and valve structure for increasing the flow rate of infusion medium into a pumping chamber and inhibiting backflow of infusion medium from the pumping chamber. In yet further embodiments, the diameter of the piston portion may be reduced and/or the diameter of the piston channel in which the piston moves may be increased, to increase the flow rate of infusion medium into the pumping chamber. By accommodating an increased flow rate, the drive mechanisms may be operable with a greater variety of infusion media.

The drive mechanism 20 includes mechanical and electromagnetic components that inherently inhabit a volume of space within the housing 12. In that regard, the drive mechanism 20 can contribute to the thickness requirements of the housing 12 and, thus, to the overall thickness dimension T of the device 10. Preferred embodiments of the present invention relate to and employ drive mechanism configurations that reduce or minimize the thickness requirements of the device, without compromising drive capabilities.

The above-referenced U.S. patent application Ser. No. 10/033,722 describes features relating to the ability to reduce or minimize the device thickness dimension T, without compromising the drive capabilities. Such features can provide significant advantages with respect to patient comfort, appearance and flexibility in selecting implant locations in the body. Embodiments of the present invention may employ one or more of such features, in conjunction with other aspects of the actuator and coil cup configurations described herein for improving operation with any one of multiple types of infusion media in an implant environment.

Also in further embodiments, the device 10 is configured such that, once implanted, it functions for a relatively long period of time to administer infusion medium to the patient and periodically be replenished from outside of the patient's body. The operational life of the device 10 is, however, limited in part by the capacity of its power source and the power requirements of the device. Preferred embodiments of the device 10 employ drive mechanisms, as described below, that provide reliable pumping action and are highly efficient with respect to power consumption, to improve the operational life of the device 10. Alternatively or in addition, drive mechanisms that provide highly efficient use of power, as described below, may be operated with smaller power sources (for example, smaller batteries) which can allow the device 10 to be made smaller.

One manner of lowering the power consumption requirements of the device 10 is to employ a coaxial coil and piston pump configuration and one or more features described herein and in U.S. patent application Ser. No. 10/033,722, for making highly efficient use of electromagnetic energy. Another manner of lowering the power consumption requirements of the device 10 is to reduce the number of operations of the drive mechanism 20 required over a given period of time, by pumping reduced volumes of a higher concentration infusion medium (an infusion medium with a higher concentration of active ingredients) or pumping higher concentration volumes at reduced intervals. However, higher concentration mediums may require a greater precision in controlling the volume delivered to the patient during a drive operation, to avoid delivering too great or too small of a volume of the higher concentration medium to the patient. Accordingly further preferred drive mechanisms 20 are configured with one or more features described herein to allow delivery of controlled volumes of infusion medium and, thus, to allow sufficiently precise delivery of relatively high concentration infusion medium.

Drive Mechanism Embodiment

Figure 2:
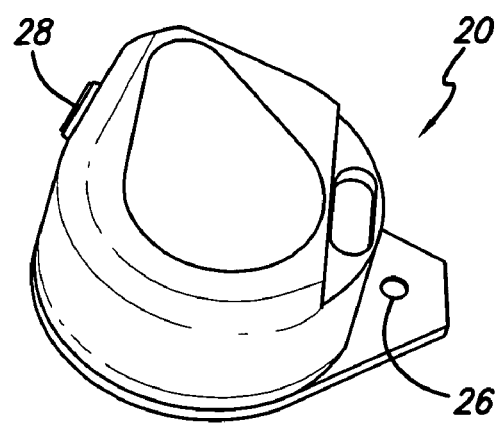
FIG. 2 is a perspective view of a drive mechanism for an implantable infusion device according to an embodiment of the invention.

FIG. 2 shows a drive mechanism 20 according to an example embodiment of the present invention. In the illustrated embodiment, the example drive mechanism 20 has a partially cylindrical, disc-shaped configuration with an inlet 26 and an outlet 28. The inlet 26 may be connected in flow communication with the reservoir portion 13 of the device 10 in FIG. 1, through suitable conduit (not shown) within the device 10. Similarly, the outlet 28 may be connected in flow communication with the outlet 16 of the device 10 in FIG. 1, through suitable conduit (not shown) within the device 10.

FIGS. 3A-D shows cross-sectional views of embodiments of the drive mechanism 20, in a retracted position or state. FIG. 4A-D show cross-sectional views of the same drive mechanism 20 embodiment, in a forward position or state. As described in more detail below, the drive mechanism 20 employs electromagnetic and mechanical forces to change (or move) between retracted and forward states, to cause infusion medium to be drawn in through the inlet 26 and forced out of the outlet 28.

Figure 5:
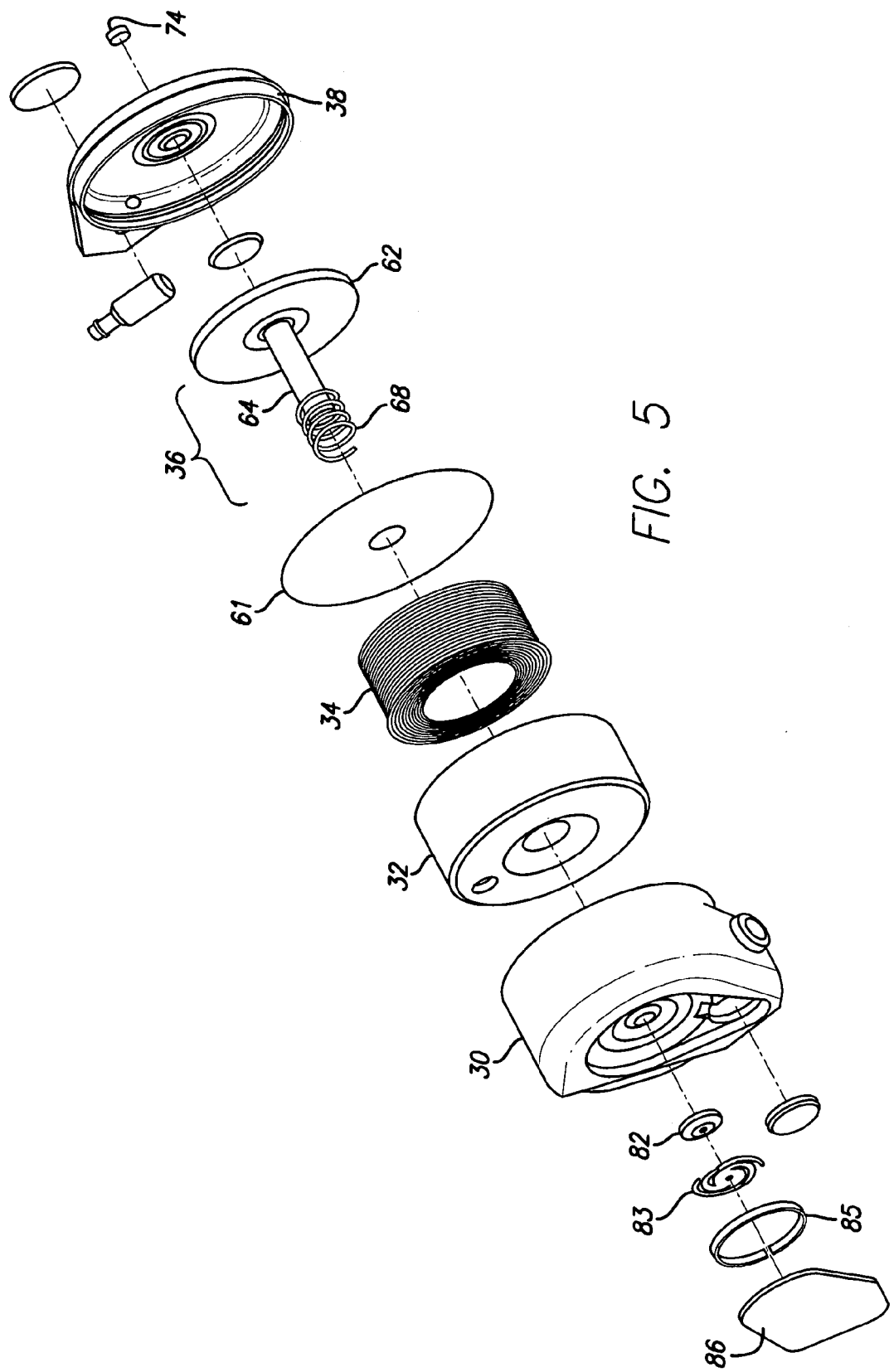
FIG. 5 is a an exploded view of an embodiment of the drive mechanism shown in FIGS. 3A-D and 4A-D.
Figure 6:
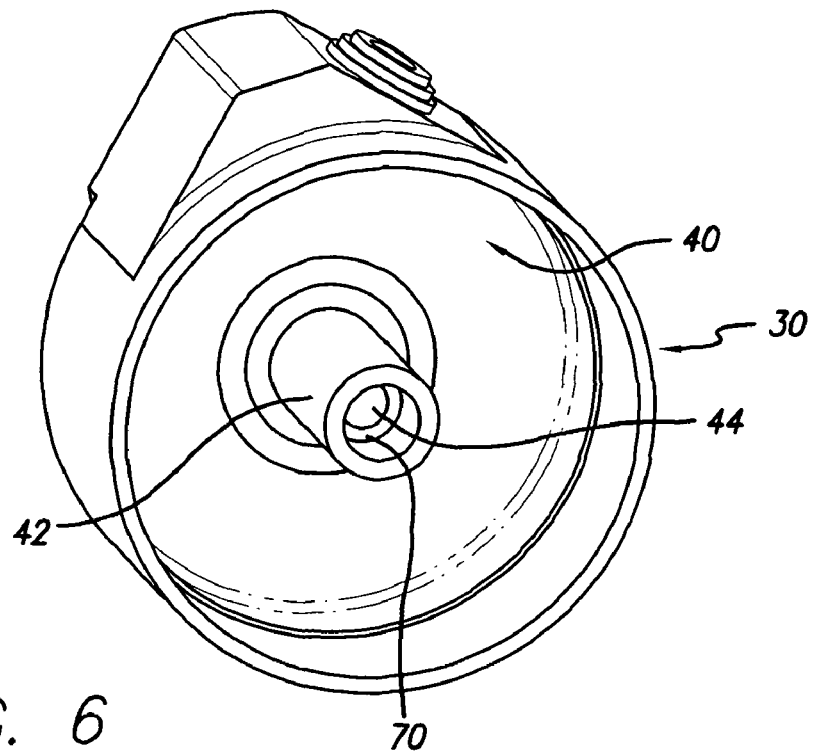
FIG. 6 is a perspective view of an embodiment of a housing member for the drive mechanism in FIGS. 3A-D and 4A-D.

The drive mechanism 20, according to one embodiment, comprises an assembly of components as shown in an exploded view in FIG. 5. Such components include a housing member 30, a coil cup 32, an electrically conductive coil 34, an actuator member 36, a cover member 38 and various other components that are described in further detail below. Some of those components are also shown in perspective views in FIGS. 6-8 and are described in more detail below.

The pump drive mechanisms 20 described herein may include, for example, various components that correspond in structure and operation to similar components of the drive mechanism described in U.S. patent application entitled "Infusion Device and Driving Mechanism For Same," Ser. No. 10/033,722, filed Dec. 27, 2001, by the owner of the present invention. However, pump drive mechanisms 20 described herein employ unique configurations relating to the actuator member 36, coil cup member 32 and related components. Such unique component configurations may be employed, for example, to improve the ability of the pump drive mechanism to operate with any one of a variety of types of infusion media, to minimize fluid stirring and fluidic resistance to actuator motion during a pump stroke and/or to simplify manufacturing processes.

While certain embodiments of the present invention employ a pump mechanism that is configured similar in many respects to pump mechanisms described in U.S. patent application Ser. No. 10/033,722, aspects of the present invention may be applicable to other pump mechanism configurations that employ an actuator and coil cup arrangement. Accordingly, other embodiments may employ other suitable pump mechanism configurations.

Housing Member for Drive Mechanism

The housing member 30 according to an example embodiment of the invention (shown in perspective view in FIG. 6) is open on one side to a hollow, annular interior section 40. The housing member 30 has a central hub portion 42 with a central piston channel 44. The bottom side of the housing member 30

(with reference to the orientation shown in FIGS. 3A-D and 4A-D), includes an opening 46 to the hollow interior section 31, through which coil wires or connection leads may pass. The bottom side of the housing member also includes a configuration of recesses and cavities for providing an outlet chamber (48 in FIGS. 3A-D and 4A-D), an outlet passage and, in some embodiments, accumulator chambers as described in the above-referenced U.S. patent application Ser. No. 10/033,722. The housing member 30 is preferably made of a generally rigid, biocompatible and infusion medium compatible material, having no or low magnetic permeability such as, but not limited to, titanium, stainless steel, biocompatible plastic, ceramic, glass or the like.

Coil Cup Member for Drive Mechanism

Figure 7A:
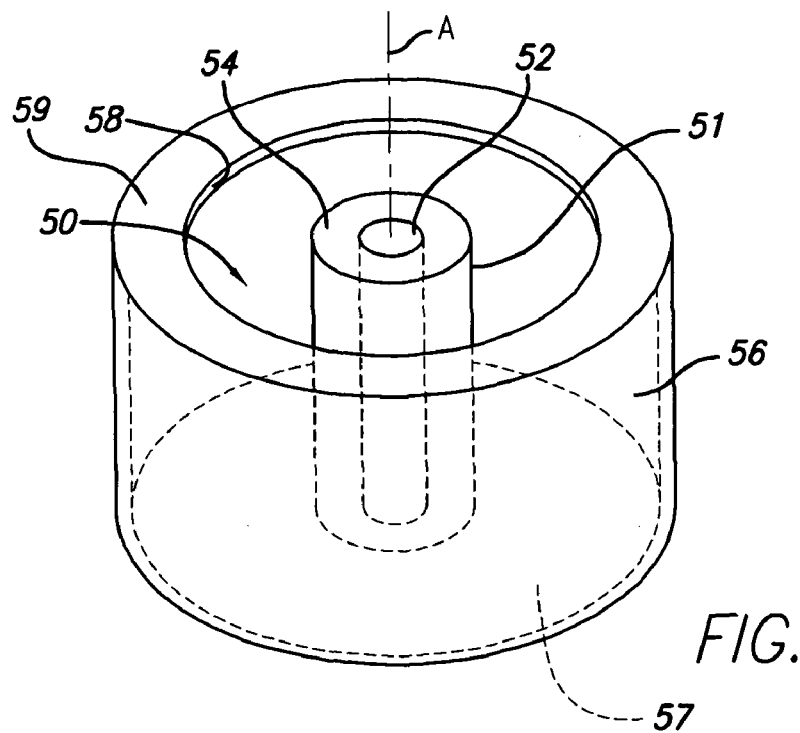
FIG. 7A is a perspective view of an embodiment of a coil cup for the drive mechanism having an outer shelf.
Figure 7B:
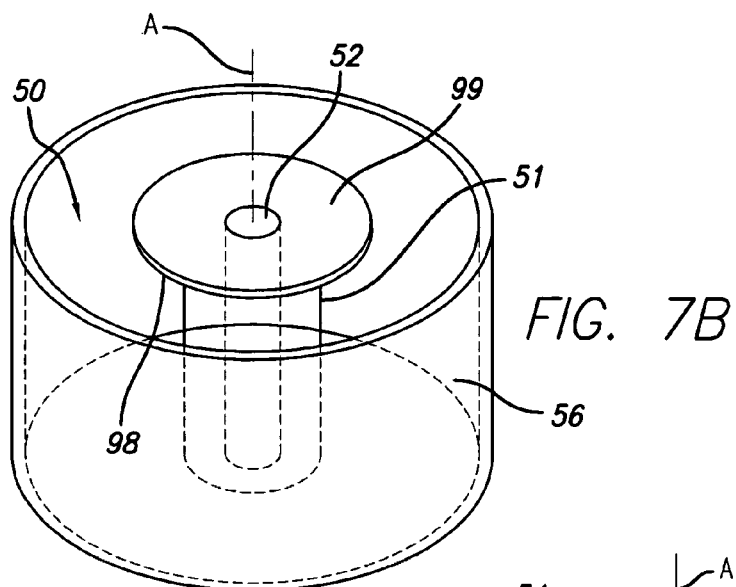
FIG. 7B is a perspective view of an embodiment of a coil cup for the drive mechanism having an inner shelf.
Figure 7C:
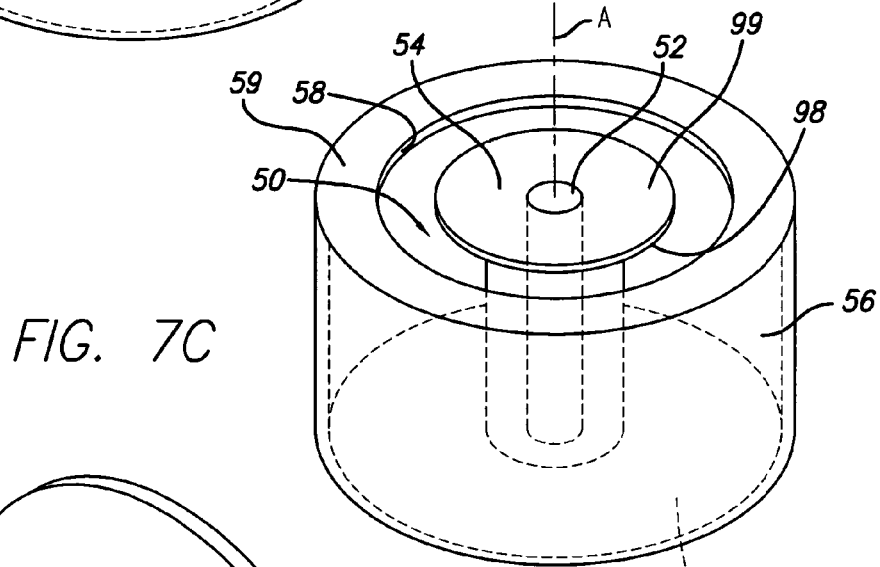
FIG. 7C is a perspective view of an embodiment of a coil cup for the drive mechanism having both an outer and inner shelf.

As shown in FIGS. 3A-D and 4A-D, the coil cup member 32 is located within the annular interior section of the housing 30. Perspective views of example embodiments of a coil cup 32 are shown in FIGS. 7A, 7B and 7C. The example coil cup member 32 has a generally cylindrical shape, with an opening 50 one side to a hollow, annular interior. The coil cup member 32 includes a central hub portion 51 having a central channel or bore 52 located axial relative to the annular interior. The hub portion 51 of the coil cup member defines an end surface 54 (or inner pole surface).

The coil cup member 32 has an outer peripheral wall 56 connected to the hub portion 51 by a backiron portion 57 of the coil cup member. In the embodiment illustrated in FIG. 3A and FIG. 7A, the coil cup member 32 also includes an annular lip or shelf 58 that extends from the outer wall 56, toward the hub portion 51, to cover a portion of the hollow interior of the coil cup member. The annular opening 50 is provided between the hub 51 and an annular, free edge of the shelf 58. The shelf 58 has a surface 59 (or outer pole surface) facing away (and upward in FIG. 7A) from the hollow interior of the coil cup member 32. As described below, the shelf 58 allows the actuator 36 to be configured with a relatively small diameter armature portion. By minimizing the diameter of the armature portion, the configuration of the armature may be simplified, thus simplifying manufacturing processes, stirring of infusion media during actuator movement may be reduced and the power usage for moving the actuator may be more efficient.

In an alternative embodiment illustrated in FIG. 7B, the coil cup member 32 may include an annular lip or shelf 98 that extends from the hub portion 51 toward the outer wall 56. The annular opening 50 is provided between the annular, free edge of the shelf 98 and the outer wall 56. The shelf 98 has a surface 99 (extending the inner pole surface 54 (see FIG. 7A)) facing away (and upward in FIG. 7B) from the hollow interior of the coil cup member 32. The embodiment of the coil cup member 32 shown in FIG. 7B may be employed with an actuator member as described in U.S. patent application Ser. No. 10/033,722. Thus, while there is no reduction in the diameter of the armature structure according to this embodiment, shelf 98 provides a larger pole area of the coil cup member 32 to increase electromagnetic flux between the pole surfaces of the coil cup member 32 and the pole surfaces of the armature.

Figure 3A:
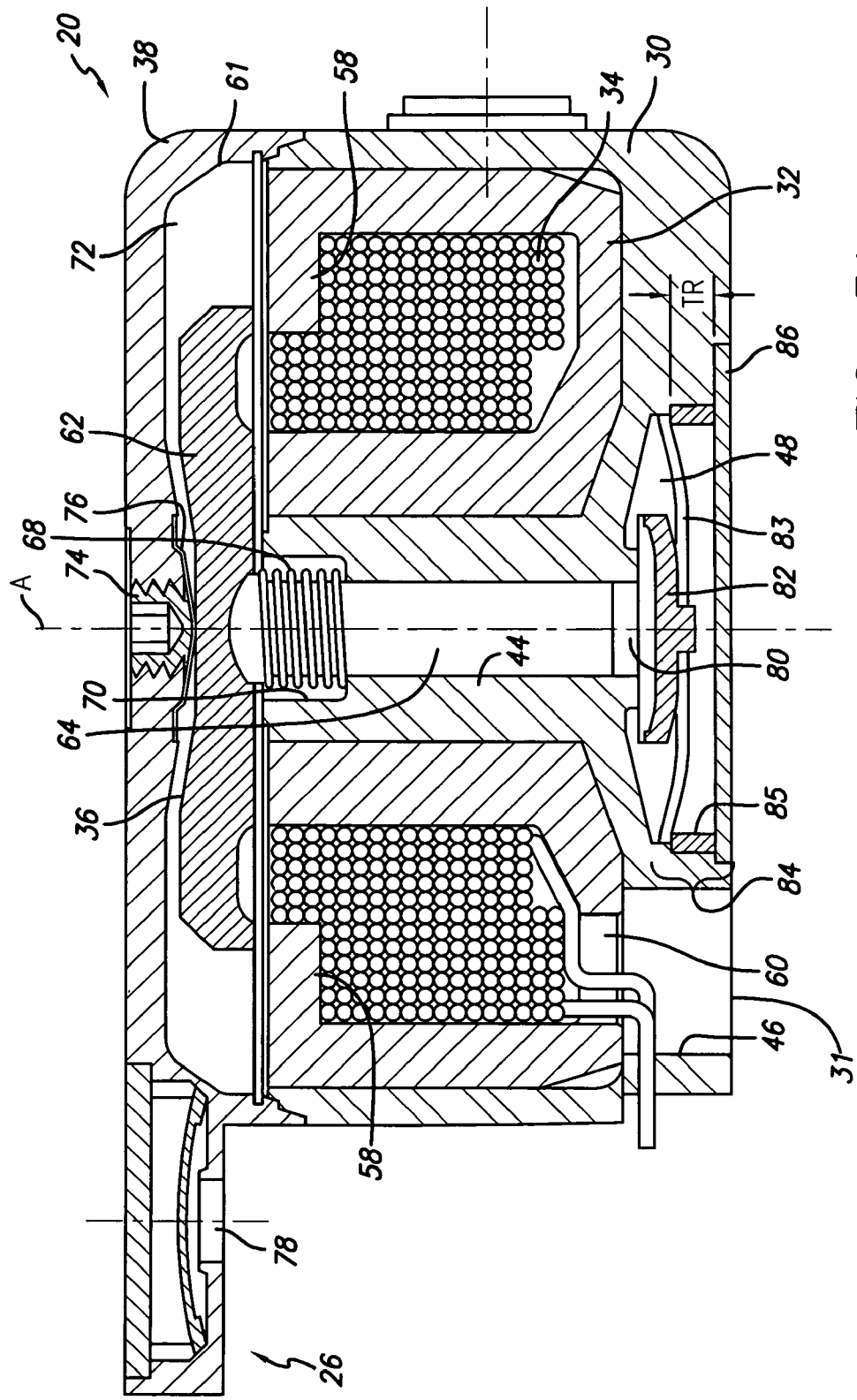
FIG. 3A is a cross-section view of one example embodiment of the drive mechanism of FIG. 2, in a retracted position or state.
Figure 3B:
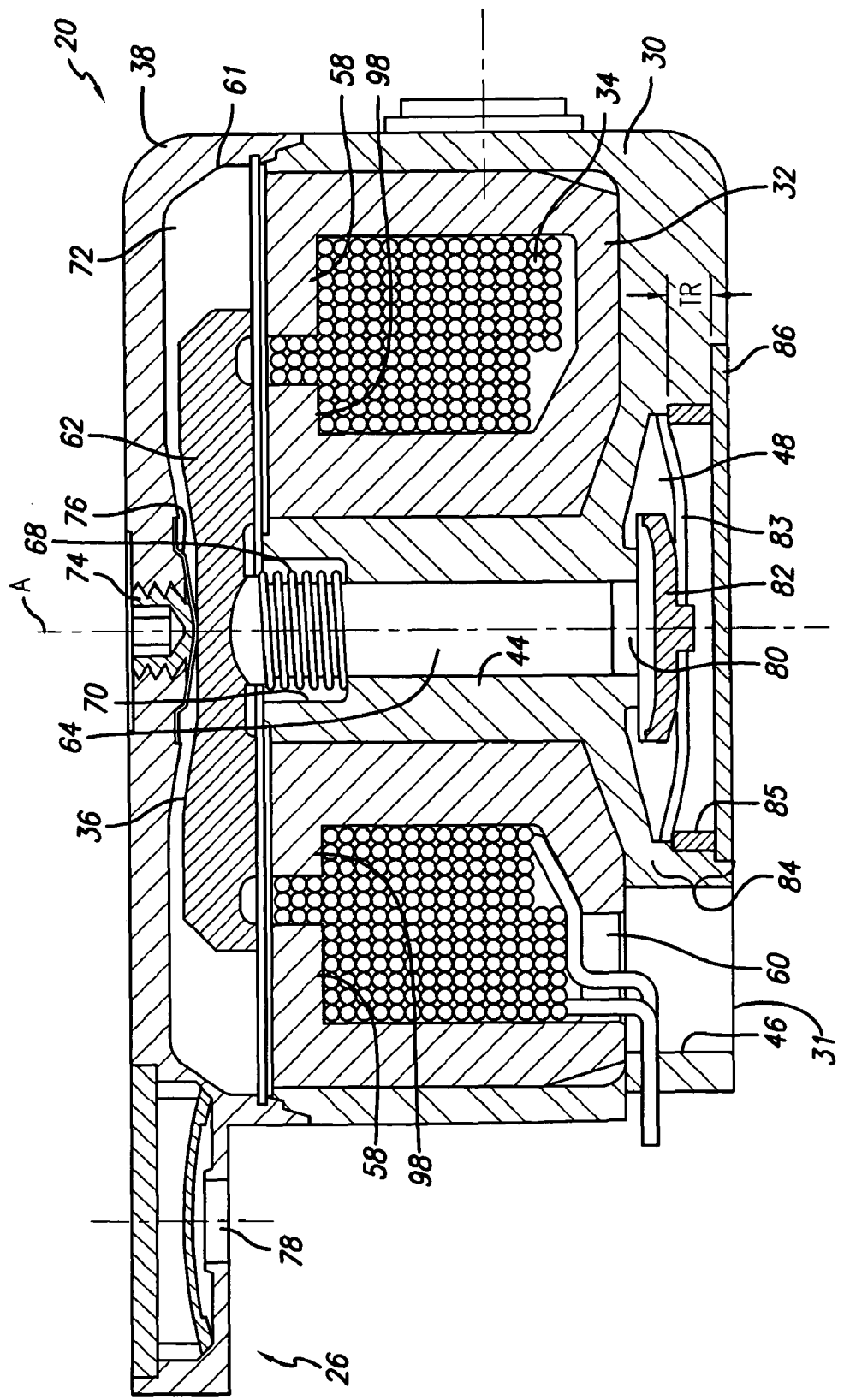
FIG. 3B is a cross-section view of one example embodiment of the drive mechanism of FIG. 2, in a retracted position or state.

In an alternative embodiment illustrated in FIG. 3B and FIG. 7C, the coil cup member 32 may include both an annular lip or shelf 58 that extends from the outer wall 56, toward the hub portion 51 and an annular lip or shelf 98 that extends from the hub portion 51 toward the outer wall 56. The annular opening 50 is provided between the annular, free edge of the shelf 98 and the annular, free edge of the shelf 58. The shelf 58 has a surface 59 (or outer pole surface) facing away (and upward in FIG. 7C) from the hollow interior of the coil cup member 32. The shelf 98 has a surface 99 (extending the inner pole surface 54 (see FIG. 7A)) facing away (and upward in FIG. 7C) from the hollow interior of the coil cup member 32. The addition of shelves 58 and 98 provides the advantages described above regarding FIGS. 7A and 7B.

In the embodiments of the present invention shown in FIGS. 3A and 3B, the minimum amount of spacing that may be provided between the outer and inner poles is determined by the distance between the outer and inner poles where fringing occurs, i.e., where the electromagnetic flux may bridge the gap between the inner and outer poles. Thus, although it is desirable to increase the areas of the poles, a minimum distance or gap must be maintained between the inner and outer poles to avoid fringing. The large surface area of the straight edges of the inner and outer poles that are opposed one to another may increase the likelihood that fringing will occur for a particular spacing between the inner and outer poles. This is because the straight edges have a large amount of surface area over which fringing may occur.

Figure 3C:
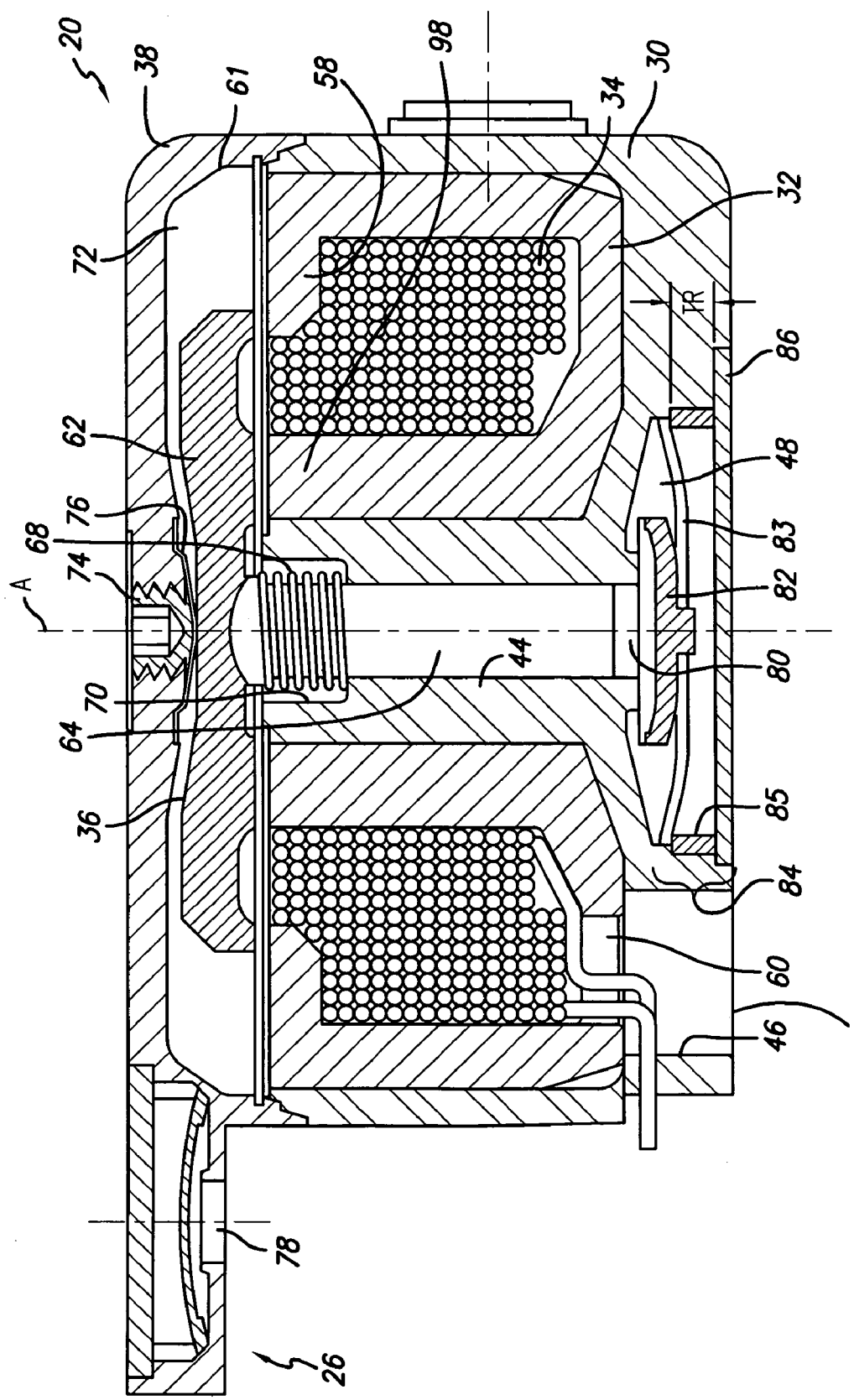
FIG. 3C is a cross-section view of one example embodiment of the drive mechanism of FIG. 2, in a retracted position or state.
Figure 3D:
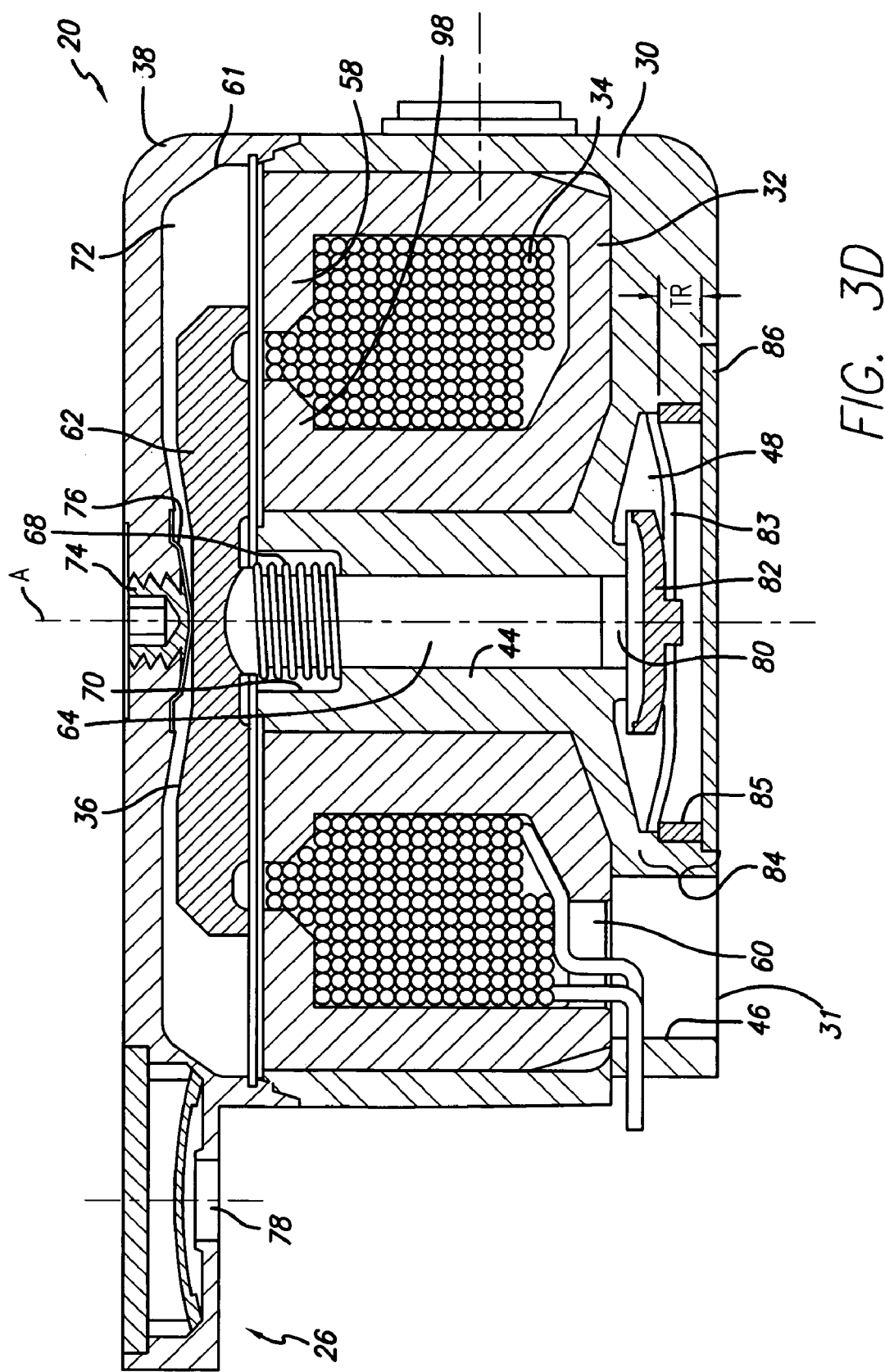
FIG. 3D is a cross-section view of one example embodiment of the drive mechanism of FIG. 2, in a retracted position or state.
Figure 4A:
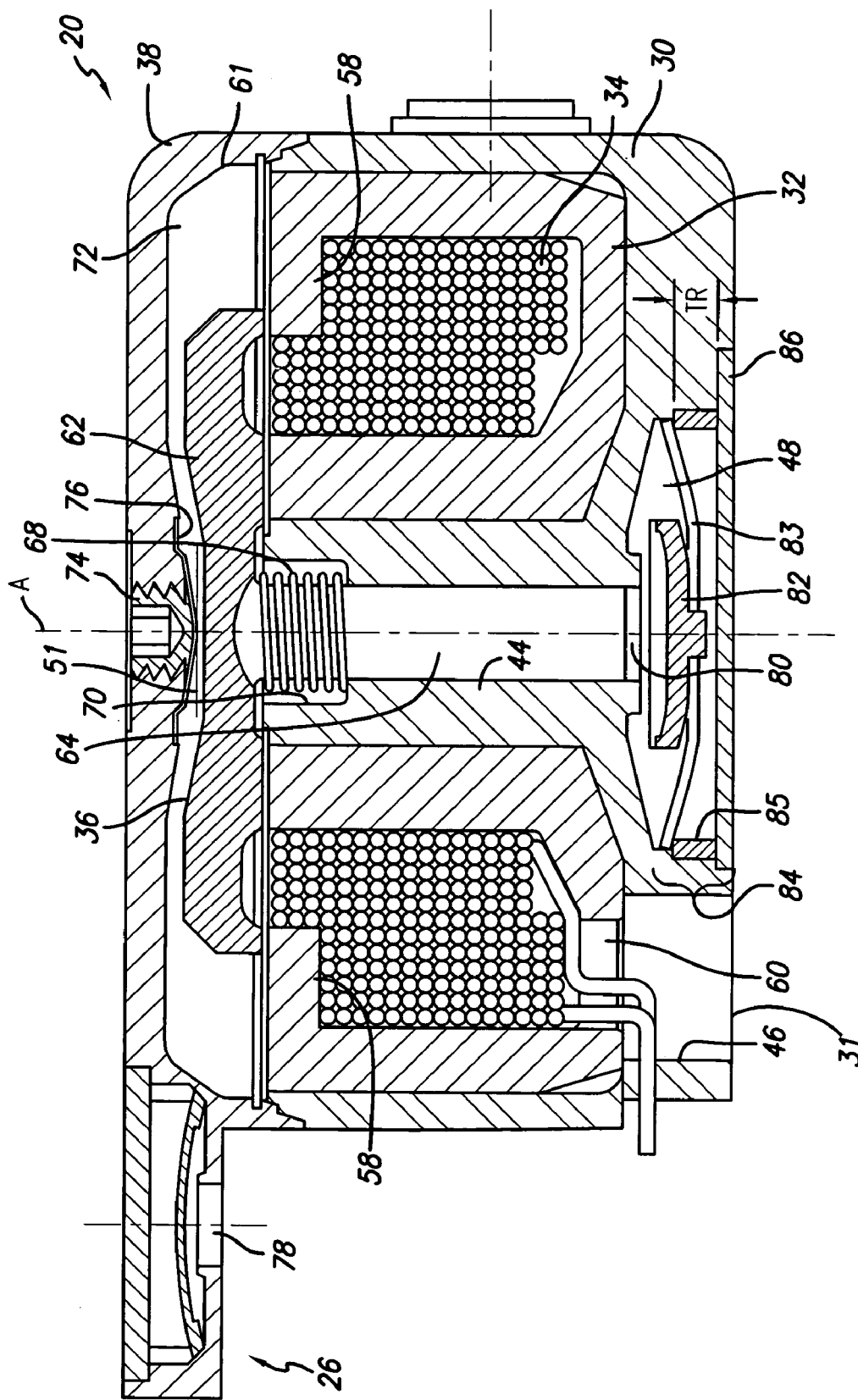
FIG. 4A is a cross-section view of the example drive mechanism embodiment of FIG. 3A, in a forward stroke position or state.
Figure 4B:
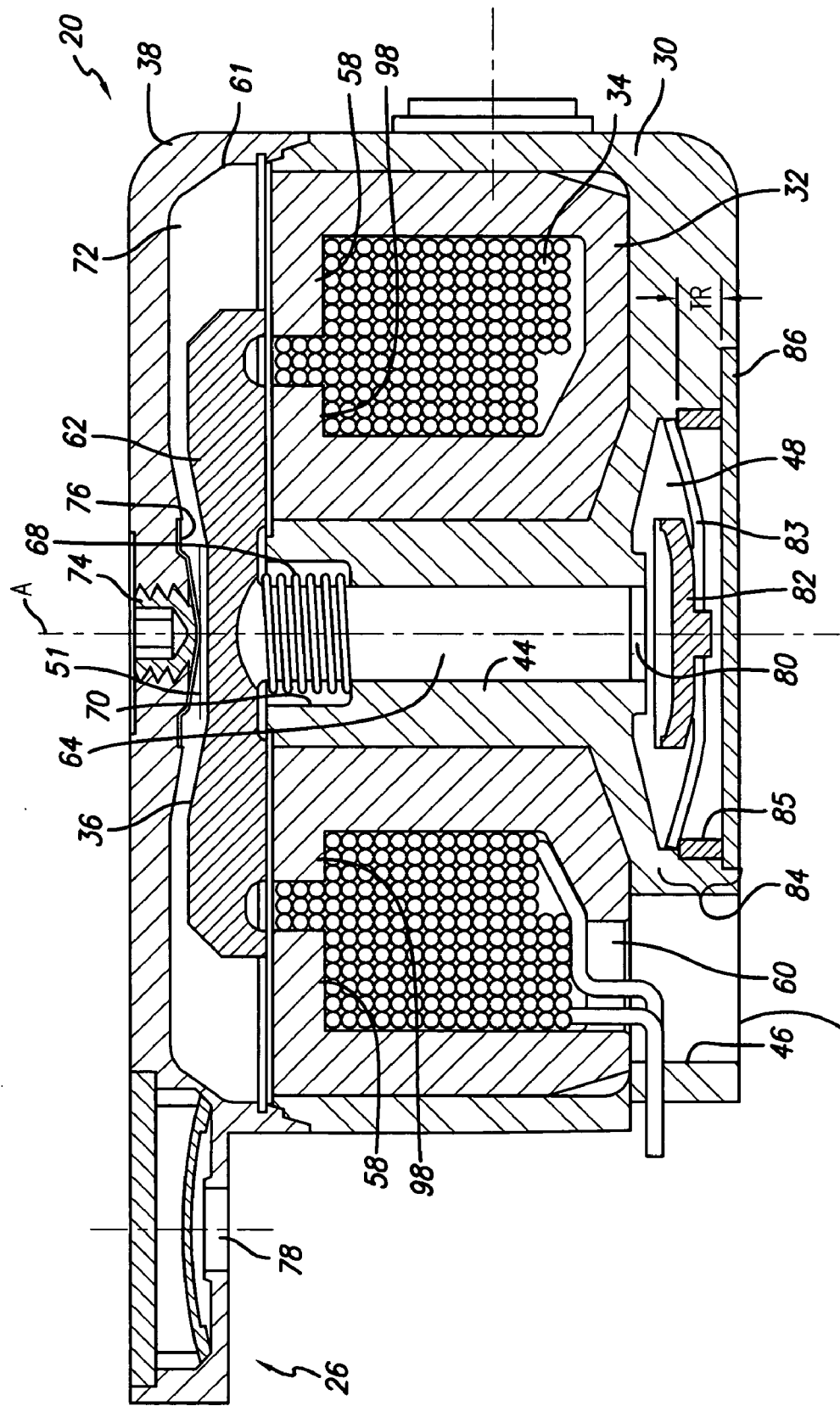
FIG. 4B is a cross-section view of the example drive mechanism embodiment of FIG. 3B, in a forward stroke position or state.
Figure 4C:
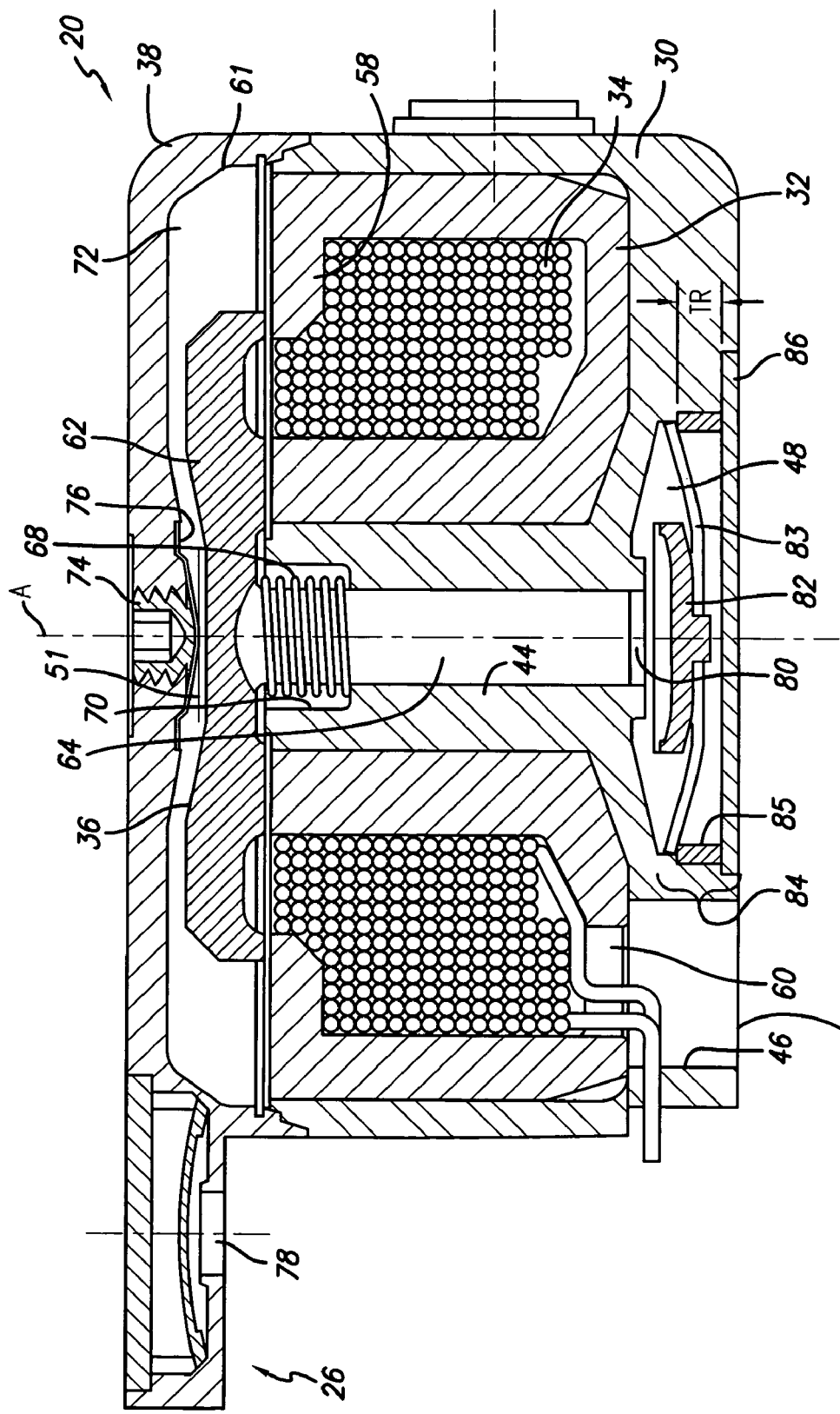
FIG. 4C is a cross-section view of the example drive mechanism embodiment of FIG. 3C, in a forward stroke position or state.
Figure 4D:
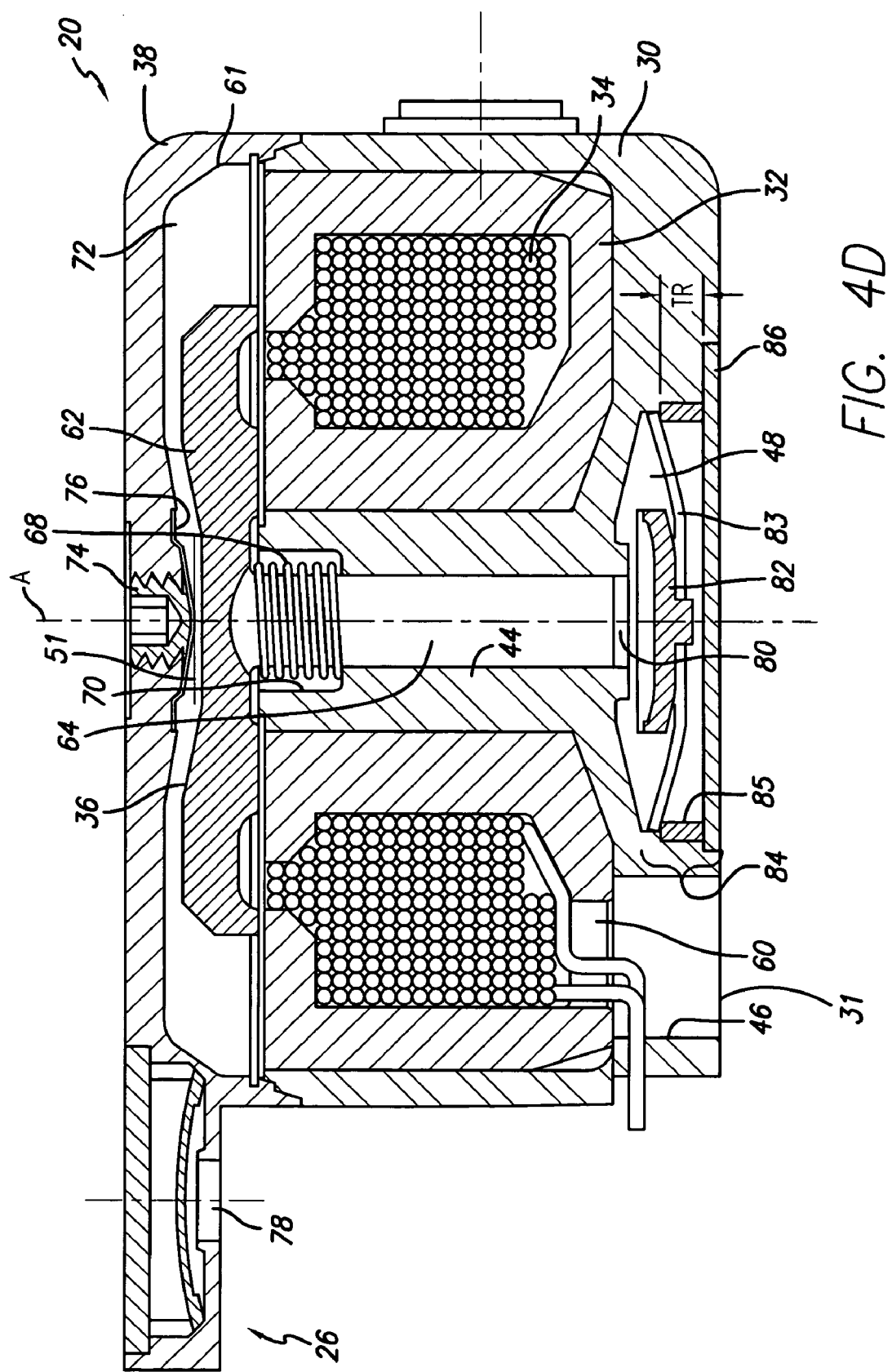
FIG. 4D is a cross-section view of the example drive mechanism embodiment of FIG. 3D, in a forward stroke position or state.

Thus, according to further embodiments of the present invention illustrated in FIGS. 3C and 3D, the inner edges of shelves 58 and 98 may be angled in order to minimize the straight surface area of the inner and outer poles that are opposed one to another in order to reduce the possibility that electromagnetic flux will bridge the gap between the inner and outer poles. Thus, a smaller gap between the inner and outer poles may be achieved.

FIG. 3C shows the shelf 58 of FIG. 3A with an angled edge. FIG. 3D shows the shelves 58 and 98 of FIG. 3B with angled edges. The edges may be formed at any suitable angle. According to embodiments of the present invention, the angle of the edge may be between approximately 10 degrees and 20 degrees. In the embodiment shown in FIG. 3D either or both of the shelves may have angled edges.

The coil cup member 32, including the shelf 58 and/or 98, is preferably made of a generally rigid material, having a relatively high magnetic permeability such as, but not limited to, low carbon steel, iron, nickel, ferritic stainless steel, ferrite, other ferrous materials, combinations thereof, or the like. As described in further detail below, at the open end of the cup member, the surfaces 54 and 59 of the hub 51 and shelf 58 (FIG. 7A) and/or surfaces 54 and 99 of the hub 51 and shelf 98 (FIG. 7B) define pole surfaces that cooperate with pole surfaces on an armature to provide a path for electromagnetic flux during a forward stroke of the drive mechanism.

The shelf 58 (and/or 98) of the coil cup member 32 may be formed as a separate, annular element, that is secured to outer wall 56 (and/or hub 51) of the coil cup member 32 by any suitable means, including, but not limited to, interference fitting, adhesive, welding, brazing or the like. By forming the shelf 58 (and/or 98) separately, the manufacturing step of placing the coil 34 in the coil cup member 32 may be simplified, because the coil 34 may be placed within the interior of the coil cup member 32, before the shelf 58 (and/or 98) is secured to the outer wall 56 (and/or hub 51). Alternatively, the shelf 58 (and/or 98) may be formed as a unitary body with the rest of the coil cup member 32, for example, in a molding or machining process.

When assembled in the pump drive mechanism, the coil cup member 32 is located in the hollow interior of the housing member 30, with the central hub portion 42 of the housing 30 extending through the central channel 52 of the coil cup 32, as shown in FIGS. 3A-D and 4A-D. The coil 34 is located within the hollow, annular interior of the coil cup member 32, and is disposed around the axis A of the annular interior of the coil cup member 32. The coil cup member 32 is provided with an opening 60, through which coil leads extend, as shown in FIGS. 3A-D and 4A-D.

The coil 34 comprises a conductive wire wound in a coil configuration. The coil wire may comprise any suitable conductive material such as, but not limited to, silver, copper, gold or the like, with each turn electrically insulated from adjacent turns and the housing. In one preferred embodiment, the coil wire has a square or rectangular cross-section, to allow minimal space between windings, thereby to allow a greater number of coil turns and, thus, improved electrical efficiency.

A biocompatible and infusion medium compatible barrier 61 may be located over the open side of the coil cup 32, between the armature portion 62 and the coil cup member 32, to maintain a gap between those two members and/or to help seal the annular interior of the coil cup and coil 34. In other embodiments in which infusion medium may contact the coil, the barrier 61 may be omitted.

Actuator Member for Drive Mechanism

Figure 8:
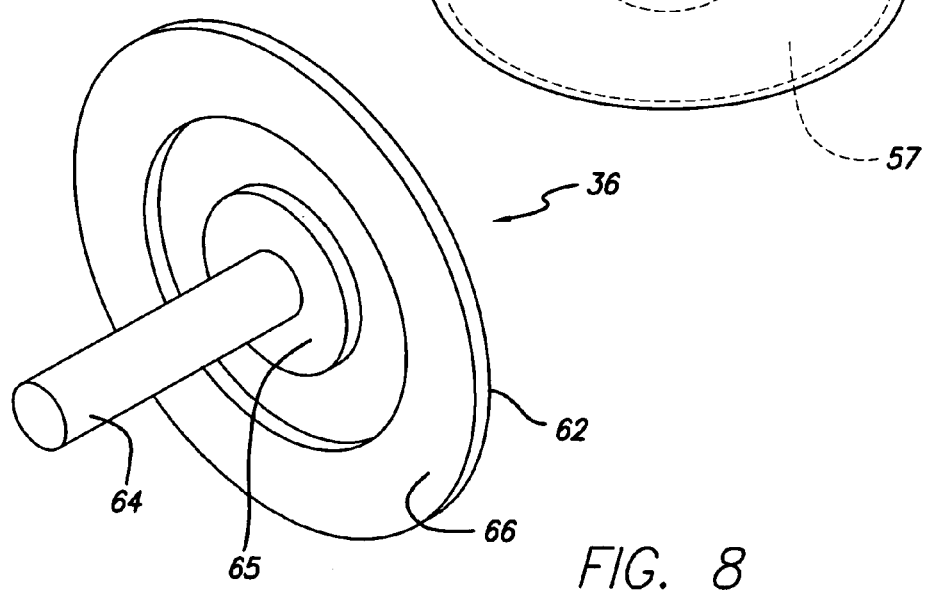
FIG. 8 is a perspective view of an embodiment of an actuator comprising an armature and a piston for the drive mechanism in FIGS. 3A-D and 4A-D.

A perspective view of an example embodiment of an actuator member 36 for the drive mechanism 20 is shown in FIG. 8. Other example embodiments of actuator members are described below with reference to FIGS. 10-12. The actuator member 36 shown in FIG. 8 is configured to operate with a coil cup member 32 having a shelf portion 58 (and/or 98) such as described above with respect to the example embodiments of FIGS. 7A, 7B and 7C. However, actuator member embodiments described below with respect to FIGS. 10-12 may be configured either to operate with a coil cup member 32 having a shelf portion 58 (and/or 98) as described above with respect to FIGS. 7A, 7B and 7C, or with a coil cup member configuration having no shelf portion as described in the above-referenced U.S. patent application Ser. No. 10/033,724.

With reference to the example embodiment shown in FIG. 8, the actuator member 36 has an armature portion 62 and a piston portion 64. In the example embodiment of FIG. 8, the armature portion 62 and the piston portion 64 of the actuator are fixed together and may be formed as a single unitary actuator structure. However, other actuator embodiments described below (with respect to FIG. 11) may employ a piston portion that is separable from the armature portion. As shown in FIG. 8, the armature portion 62 of the actuator member has a generally round, disc shaped configuration, with an annular outer section (or outer pole) 66 and an annular inner section (or inner pole) 65. The area of the inner and outer pole surfaces may be selected for optimal efficiency. For example, the inner pole surface area may be about 0.02937 square inches, while the outer pole surface area may be about 0.05347 square inches. Other embodiments may employ other suitable pole surface areas.

As described in more detail below, the armature portion 62 cooperates with the pole surfaces 54, 59 and/or 99 of the coil cup member 32, to provide a flux path for electromagnetic flux. In addition, the armature portion 62 of the actuator 36 is located in a volume of the pump mechanism 20, in which it is in direct contact with infusion medium to be pumped to the patient. Accordingly, the armature portion 62 of the actuator 36 is preferably made of a generally rigid material, having a relatively high magnetic permeability such as, but not limited to, ferrous materials such as S44700 stainless steel (ASTM A276-98b) or the like.

In addition, in preferred embodiments, the ferrous material of the armature portion 62 is suitably covered with a biocompatible and infusion medium compatible material, such as titanium or titanium alloy cladding. Titanium can exhibit a relatively high level of corrosion resistance and compatibility with a large variety of infusion media. Accordingly, embodiments of the invention may employ a titanium or titanium alloy coating on the armature portion (and other portions of the pump drive mechanism that come into direct contact with the infusion medium), to allow operation with any one of a variety of different types of infusion media. For example, embodiments of the invention may employ a layer of about 1.5 mils to about 3.0 mils of titanium or titanium alloy on a ferrous armature portion 62. However, other embodiments may employ other suitable cladding thicknesses and other suitable coating materials that provide a sufficient resistance to and compatibility with a variety of types of infusion media, including, but not limited to, carbon coating, gold, platinum, diamond, titanium nitride or other ceramic material. Such coatings may be applied in any suitable manner, including, but not limited to electrochemical or electromagnetic deposition, dipping or applying liquid cladding materials that solidify on the actuator, or the like.

In one example embodiment (not shown), the armature portion 62 of the actuator member 36 is provided with a plurality of apertures and radial struts as described in further detail in the above-referenced U.S. patent application Ser. No. 10/033,722. Such apertures allow the armature portion of the actuator to move within a volume of fluidic infusion media with reduced resistance from the fluid (by allowing fluid to pass through the apertures during actuator movement). The radial struts complete the flux path between the inner and outer poles of the armature portion 62.

However, such apertures and struts in the armature portion can increase the manufacturing complexity, especially if the magnetically permeable material of the armature portion 62 is to be clad with a titanium, titanium alloy or other suitable cladding material. In particular, it can be difficult to sufficiently clad all exposed surfaces of an armature portion having such apertures and radial struts. Accordingly, further embodiments employ an armature portion 62 that is free of apertures and radial struts. Yet other embodiments employ a relatively small number of apertures.

Without apertures (or with a reduced number of apertures), the problems associated with fluidic resistance and stirring of the infusion media noted above may be encountered. Accordingly, embodiments employing armature portions 62 with no or minimal apertures are preferably configured with a reduced diameter. The reduced diameter of the armature portion 62 results in less fluidic resistance, because the armature has less surface area in contact with the infusion medium and displaces less volume of the infusion medium during actuator movement. Alternatively, instead of reducing the armature diameter, the diameter dimensions of the coil, coil cup member and housing may be increased relative to the diameter of the armature portion 62, to increase electromagnetic power applied to the armature. However, such an alternative embodiment may result in increased power consumption and increased dimensions of the pump mechanism. Thus, embodiments employing a reduced diameter armature portion 62 may be preferred in implant environments, in which minimizing size and maximizing power usage efficiency are typically important.

Figure 14A:
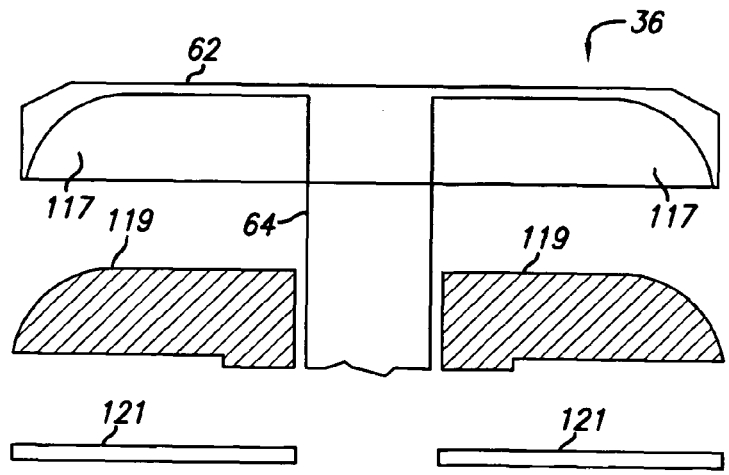
FIG. 14A is a simplified cross-section diagram, showing an unassembled armature according to embodiments of the present invention.
Figure 14B:
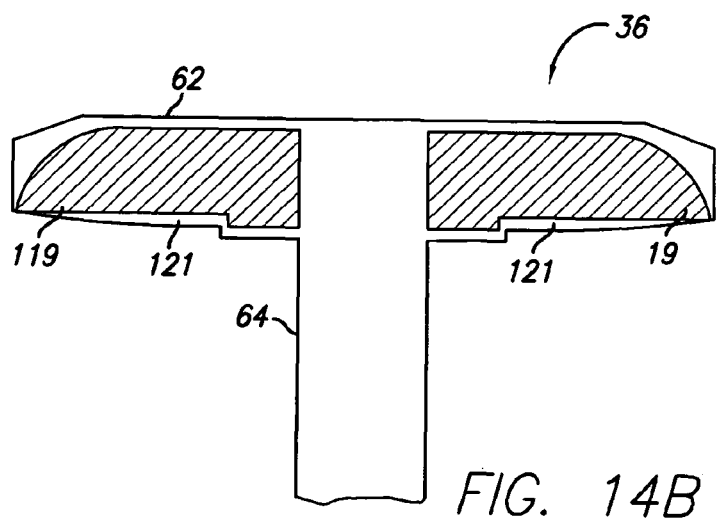
FIG. 14B is a simplified cross-section diagram, showing an assembled armature according to embodiments of the present invention.
Figure 15:
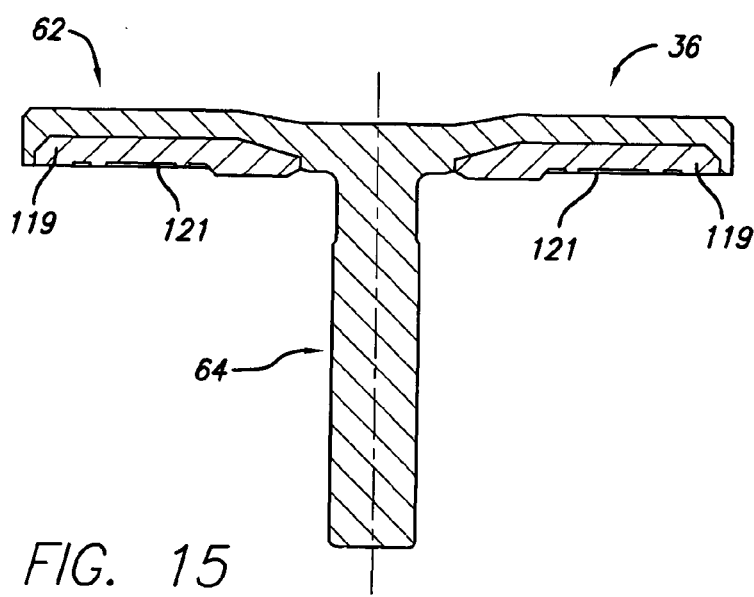
FIG. 15 is a simplified cross-section diagram, showing an assembled actuator including an armature and a piston, according to embodiments of the present invention.

According to further embodiments of the present invention, the armature portion 62 of the actuator 36 may be manufactured from any suitable material, including materials having a low magnetic permeability. According to these embodiments, as shown in FIGS. 14A, 14B and 15, armature portion 62 of the actuator 36 may be formed with a cavity 117 into which a material 119 may be placed. Material 119 may be any suitable material having a relatively high magnetic permeability such as, but not limited to, ferrous materials such as S44700 stainless steel or the like. A cover 121 made from a material such as, but not limited to, a foil material, may then be placed over the cavity 117 to provide a cover for material 119. FIG. 14A shows armature portion 62, material 119 and cover 121 in an unassembled state. FIG. 14B shows armature portion 62, material 119 and cover 121 in an assembled state. FIG. 15 shows an assembled actuator 36 (including the armature portion 62 and the piston portion 64) having a cavity 117 into which a material 119 is placed and covered with cover 121, according to an embodiment of the present invention. The material 119 may be chosen to have any suitable dimensions.

By providing a cavity in the armature portion 62 of the actuator 36 in which to place and cover the relatively high magnetic permeability material, contact between the relatively high magnetic permeability material and the infusion medium is minimized. The relatively high magnetic permeability material provides a flux path for electromagnetic flux, so that the remainder of the armature portion 62 need not do so. Thus, the remainder of the armature portion 62 may be manufactured from any suitable biocompatible and infusion medium compatible material, having no or low magnetic permeability such as, but not limited to, titanium, stainless steel (which may be ferritic or non-ferritic), biocompatible plastic, ceramic, glass or the like.

When assembled (as shown in FIGS. 3A-D and 4A-D), the armature portion 62 of the actuator member 36 resides adjacent the open end of the coil cup member 32 and the piston portion 64 of the actuator member 36 extends into the piston channel 44 of the housing member 30. As described above, the armature portion 62 of the actuator member 36 includes a magnetically permeable material. This allows the armature to electromagnetically cooperate with the coil cup member 32 and form a flux path, upon electrical energization of the coil 34.

More specifically, the armature portion 62 is provided with an annular inner pole surface 65 and an annular outer pole surface 66. In the illustrated embodiments, the annular pole surfaces 65 and 66 are raised relative to the rest of the armature portion 62, for example, to allow for a greater amount of magnetically permeable material to be present at the pole locations. However, in other embodiments, the pole surfaces may be in plane with the rest of the armature portion or recessed relative to the rest of the armature portion.

A simplified, cross-sectional diagram of the coil cup member 32 and the actuator member 36 illustrated in FIG. 3A, in their assembled orientation, is shown in FIG. 9. As described in more detail below, the inner and outer pole surfaces 65 and 66 of the armature portion 62 align with the inner and outer pole surfaces 54 and 59 of the coil cup member 32 to allow a flux path F to be formed, when the coil 34 is energized. Upon energization of the coil 34, the flux path F is formed through the outer peripheral wall 56 of the coil cup member 32 and across a gap between the outer pole surface 59 of the coil cup member 32 and the outer pole surface 66 of the armature portion 62. The flux path F continues through the armature portion 62, across the gap between the inner pole surface 65 of the armature portion 62 and the inner pole surface 54 of the coil cup member 32. The circuit of the flux path F is completed through the hub portion 51 and backiron 57 of the coil cup member 32, and back to the outer peripheral wall 56 of the coil cup member 32. Although not described in detail, embodiments of the present invention illustrated in FIGS. 3B-D operate in a similar manner to that described for the embodiment illustrated in FIG. 3A.

As shown in FIG. 9, by employing a coil cup member 32 with a shelf 58 extending toward the hub 51, the outer pole 66 of the armature portion 62 need not extend to the outer wall 56 to provide the flux path F. Instead, a portion of the flux path F can be provided through the shelf 58. In this manner, the diameter D of the armature portion 62 may be minimized, for example, to simplify manufacturing processes, reduce stirring of infusion media during actuator movement and/or make more efficient use of power. Alternatively, the shelf 58 may be employed to allow the diameter of the coil cup member 32 to be increased, without requiring a like increase in the diameter of the armature portion 62.

In the embodiment shown in FIG. 9, the relative dimensions of the armature portion 62, coil cup member 32 and shelf 58 are selected such that the outer pole 66 of the armature portion 62 overlaps a portion of the shelf 58. A gap is provided between the outer pole 66 of the armature portion 62 and the shelf 58. Similarly, a gap is provided between the inner pole 65 of the armature portion 62 and the inner pole surface 54 of the coil cup member 32.

In some embodiments, the armature portion 62 and/or the coil cup member 32 may be configured such that the gap between the outer pole surface 66 of the armature portion 62 and the outer pole surface 59 of the coil cup member 32 is greater than the gap between the inner pole surface 65 of the armature portion 62 and the inner pole surface 54 (FIG. 7A) of the coil cup member, when the actuator is in the retracted position shown in FIGS. 3A-D. A greater outer pole spacing, relative to the inner pole spacing, can result in reduced residual flux that could otherwise cause the armature to stick in the forward position (the FIGS. 4A-D position). In addition, a greater outer pole spacing reduces the squeezing effect on infusion medium between the outer pole 66 of the armature portion 62 and the shelf 58, as the armature portion 62 moves toward the forward position during actuation of the pump mechanism.

As described in more detail below, the energization of the coil 34 creates an electromagnetic force on the armature portion 62 of the actuator 36, to draw the armature portion 62 toward the coil cup member 32 (i.e., to close the gaps between the inner pole surfaces 54 and 65 and between the outer pole surfaces 59 and 66). By drawing the armature portion 62 of the actuator member 36 toward the coil cup member 32, the piston portion 64 of the actuator member 36 is forced further into the piston channel 44, toward the outlet chamber of the housing member 30. This action effects a forward stroke of the drive mechanism 20, as shown in FIGS. 4A-D. Upon sufficient de-energization of the coil 34, the actuator member 36 is forced toward a retracted position, as shown in FIGS. 3A-D, for example, by the force of a spring 68, a magnet (not shown) or both.

The actuator spring 68 in the illustrated embodiment comprises a coil spring disposed around the piston portion 64 of the actuator member 36, adjacent the armature portion 62 of the actuator member 36. One end of the coil spring abuts the armature portion 62 of the actuator, while the opposite end of the coil spring abuts a shoulder 70 in the piston channel 44 of the housing member 30. In this manner, the actuator spring 68 imparts a spring force between the housing member 30 and the actuator member 36, to urge the actuator member 36 toward its retracted position shown in FIG. 3A-D.

In the illustrated embodiment, by using a coil spring 68 located around and coaxial with the piston portion 64 and disposed partially within the piston channel 44, the actuator spring may have minimal or no contribution to the overall thickness dimension of the drive mechanism. However, in other embodiments, actuator springs may have other suitable forms and may be located in other positions suitable for urging the actuator toward its retracted position shown in FIGS. 3A-D. The actuator spring 68 is preferably made of a biocompatible and infusion medium compatible material that exhibits a suitable spring force such as, but not limited to, titanium, stainless steel, MP35N cobalt steel or the like. In further embodiments, a magnet may be arranged to provide a return force on the actuator, either in addition to or as an alternative to the actuator spring 68, to return the actuator to its retracted position. An example of a magnet arranged for providing a return force on an actuator is described in U.S. patent application Ser. No. 10/033,724.

Cover Member for Drive Mechanism

The cover member 38 of the drive mechanism 20 attaches to the housing member 30, to cover the open side of the housing member, the armature portion 62 and the barrier 61. The cover member 38 is preferably made of a generally rigid, biocompatible and infusion medium compatible material, having a relatively low magnetic permeability (being relatively magnetically opaque) such as, but not limited to, titanium, stainless steel, biocompatible plastic, ceramic, glass or the like.

The cover member 38 defines an interior volume 72 between the barrier 61 and the inner surface of the cover member. The armature portion 62 of the actuator member 36 resides within the interior volume 72 when the cover is attached to the housing, as shown in FIGS. 3A-D and 4A-D. As described below, the armature portion 62 of the actuator 36 is moveable in the axial direction A within the volume 72, between a retracted position shown in FIGS. 3A-D and a forward stroke position shown in FIGS. A-D. This movement is created by the action of electromagnetic force generated when a current is passed through the coil 34 and by the mechanical return action of the actuator spring 68.

An adjusting plunger 74 may be located within the cover member 38, for contacting the armature portion 62 of the actuator 36, when the armature portion 62 is in the fully retracted position shown in FIGS. 3A-D. The adjusting plunger 74 may be used to set the retracted position of the armature portion 62. A seal may be disposed between the plunger 74 and the cover member 38, for example, but not limited to, a silicon rubber sealing ring. In further embodiments, a flexible diaphragm 76 (such as, but not limited to, a thin titanium sheet or foil) may be coupled to the inside surface of the cover member 38 and sealed around the opening through which the plunger 74 extends. The diaphragm will flex to allow the plunger to define an adjustable retracted position and, yet, provide sealing functions for inhibiting leakage at the interface between the plunger 74 and the cover member 38. In further embodiments, once a proper armature position is set, the plunger may be fixed in place with respect to the cover member, for example, by adhering the plunger to the cover member with one or more welds, adhesives or other securing methods.

The cover member 38 includes the inlet 26 of the drive mechanism, which has an inlet opening 78 in fluid flow communication with the interior volume 72. The inlet opening 78 connects in fluid flow communication with the reservoir of the infusion device 10 (FIG. 1), to receive infusion medium from the reservoir. Connection of the inlet opening 78 and the reservoir may be through suitable conduit (not shown), such as tubing made of or coated with suitable infusion medium compatible material, including, but not limited to titanium, stainless steel, biocompatible plastic, ceramic, glass or the like. In a further embodiment, the tubing is made of or coated with a material selected to be compatible with a variety of infusion media, such as, but not limited to titanium, titanium alloy, stainless steel, or the like.

Piston Channel and Outlet Chamber for Drive Mechanism

As shown in FIGS. 3A-D and 4A-D, the piston portion 64 of the actuator member 36 extends through the axial piston channel 44 in the housing member 30, toward the outlet chamber 48 at the end of the piston channel 44. The channel 44 has an inside diameter which is larger than the outside diameter of the piston portion 64. As a result, an annular volume is defined between the piston portion 64 and the wall of the piston channel 44, along the length of the piston channel 44. Infusion medium may flow through the annular volume, from the volume 72 within the cover member 38 to a piston chamber 80 located between the free end of the piston portion 64 and a valve member 82 of a valve assembly 84.

In some example embodiments of the invention, the radial spacing between the piston portion 64 and the wall of the piston channel 44 is selected to be large enough to provide a suitable flow of infusion medium toward the pumping chamber 80 to refill the pumping chamber 80 (during a return stroke of the piston portion), but small enough to sufficiently inhibit back flow of medium from the pumping chamber 80 (during a forward stroke of the piston portion).

The actual radial spacing between the piston portion 64 and the wall of the channel 44 to achieve such results depends, in part, on the overall dimensions of those components, the pressure differentials created in the mechanism and the viscosity of the infusion medium. For example, the radial spacing may be selected such that the volume of medium for refilling is between about 1 and 4 orders of magnitude (and, more preferably, about 2 orders of magnitude) greater than the volume of medium that backflows through the space. Alternatively, or in addition, the radial spacing may be defined by the ratio of the diameter $D_P$ of the piston portion 64 the diameter $D_C$ of the channel 44, where the ratio $D_P/D_C$ is preferably within a range of about 0.990 to about 0.995. As a representative example, a total spacing of about 400 to 600 micro-inches or less and, preferably, an average radial gap of about 250 micro-inches annularly around the piston portion 64 may be employed. In further embodiments described below with reference to FIGS. 10-12, other relative dimensions between the piston portion and pumping channel may be employed.

The valve assembly 84 in the embodiment of FIGS. 3A-D and 4A-D includes the valve member 82, a valve spring 83 and support ring 85. The valve member 82 is located within the outlet chamber 48 and, as shown in FIGS. 3A-D, is positioned to close the opening between the axial piston channel 44 and the outlet chamber 48, when the actuator member 36 is in the retracted position. In FIGS. 4A-D, the valve member 82 is positioned to open a flow passage between the axial piston channel 44 and the outlet chamber 48. The valve spring 83 is located within the outlet chamber 48, to support the valve member 82. The spring 83 imparts a spring force on the valve member 82, in the direction toward piston 64, urging the valve member 82 toward a closed position, to block the opening between the axial channel 44 and the outlet chamber 48.

The valve member 82 and the support ring 85 are preferably made of a generally rigid, biocompatible and infusion medium compatible material, such as, but not limited to, titanium, stainless steel, biocompatible plastic, ceramic, glass, gold, platinum or the like. In a further embodiment, the valve member and ring are made of or clad with a material selected to be compatible with a variety of infusion media, such as, but not limited to titanium or titanium alloy, or the like.

A layer of silicon rubber or other suitable material may be attached to the rigid valve member material, on the surface facing the channel 44, to help seal the opening to the channel 44 when the valve member is in the closed position shown in FIGS. 3A-D. Various alternative valve assembly configurations may be employed with embodiments of the present invention, including, but not limited to such configurations as described in co-pending U.S. patent application Ser. No. 10/033,722.

The valve spring 83 is preferably made of a biocompatible and infusion medium compatible material that exhibits a suitable spring force such as, but not limited to, titanium, stainless steel, MP35N cobalt steel or the like. In a further embodiment, the spring is made of or clad with a material selected to be compatible with a variety of types of infusion media, such as, but not limited to titanium, titanium alloy, stainless steel, or the like.

In the illustrated embodiment, the outlet chamber 48 comprises a cavity in the bottom of the housing 30, as shown in FIGS. 3A-D and 4A-D. The outlet chamber cavity 48 may be provided in flow communication with an outlet 28 (FIG. 2), through a flow passage (not shown). The outlet flow passage may include one or more accumulator cavities provided with accumulators, as described in the above-referenced U.S. patent application Ser. No. 10/033,722, for example, to help stabilize the flow rate of the drive mechanism, help provide a relatively constant output pressure during drive operations, and minimize backflow down axial channel 44.

Manufacturing Process for Drive Mechanism

A drive mechanism as shown in FIGS. 3A-D and 4A-D may be constructed by providing components as shown in FIG. 5 and assembling the components in any suitable sequence. The components may be made according to any suitable process including, but not limited to molding, machining, extruding, sintering, casting, combinations thereof or the like.

The coil 34 may be inserted into the annular interior of the coil cup member 32, with the coil leads extended through a coil lead opening 60 in the coil cup. The coil may be impregnated or partially impregnated with a fill material of epoxy or the like, for adhering the coil to the coil cup and for sealing or partially sealing the coil. The fill material may also be used to adhere the barrier plate 61 to the coil members, to avoid warping or bulging of the barrier plate after assembly.

The coil cup member 32 and coil 34 may be inserted into the interior 40 of the housing member 30, with the coil leads or connectors (which may be wire leads or flexible conductive tabs) extending through a coil lead opening 46 in the housing member 30. In preferred embodiments, the coil cup and housing members are configured to provide a tight, friction fit therebetween, without requiring additional means of adhering the two components together. In other embodiments, the coil cup and housing members may be coupled together by any suitable adhesive material or other adhering methods, including, but not limited to welding, brazing, of the like.

The barrier 61 may be placed over the coil, coil cup and housing sub-assembly. The barrier 61 may be adhered to the housing by one or more adhering points or continuously along the circumference of the barrier 61, with any suitable adhesive material or other adhering methods, including, but not limited to welding, brazing, soldering or the like. Alternatively, or in addition, the barrier 61 may be held in place by a shoulder portion of the cover member 38. In addition, as noted above, the barrier 61 may be adhered to the coil 34 by fill material in the coil. In preferred embodiments, the barrier 61 is held in a generally flat relation relative to the coil cup member and coil. To enhance this flat relation, the coil cup and housing members may assembled together and then machined to planarize the barrier contact surfaces, prior to inserting the coil in the coil cup and prior to adding fill material to the coil.

Once the barrier 61 is placed over the coil, coil cup and housing members, the actuator member 36 may be added to the sub-assembly. First, however, the actuator spring 68 is placed around the piston portion 64, adjacent the armature portion 62 of the actuator member 36. Then the free end of the piston portion 64 is inserted into the axial channel 44 of the housing member 30, with the armature end of the actuator member 36 arranged adjacent the barrier 61.

The cover member 38 may then be disposed over the armature end of the actuator member 36 and secured to the housing member 30. In preferred embodiments, the cover member 38 is adhered to the housing member 30 by one or more adhering points or continuously along the circumference of the cover member 38, with one or more welds or any other suitable adhering methods, including, but not limited to adhesive materials, brazing or the like.

The valve side of the drive mechanism may be assembled before or after the above-described components are assembled. On the valve side of the drive mechanism, the valve member 82 is disposed within the outlet chamber cavity 48 of the housing member 30. The valve spring 83 and ring 85 are disposed within the outlet chamber cavity 48, adjacent the valve member 82. Any suitable number of accumulators may be placed within each of the accumulator cavities (not shown). A valve cover 86 may then be placed over the outlet chamber cavity 48 and accumulator cavities. The valve cover 86 may be adhered to the housing member 30 by one or more adhering points or continuously along the circumference of the valve cover, with one or more welds or any other suitable adhering methods, including, but not limited to adhesive materials, brazing or the like.

The volume of the pumping chamber 80, the compression of the actuator spring 68 and the position of the actuator 36 in the retracted position shown in FIGS. 3A-D may be adjusted by the adjusting the position of the adjusting plunger 74. Adjustments of the plunger 74 may be made during manufacture and the adjusted position may be fixed by welding or otherwise adhering the plunger 74 in the adjusted position during manufacture. In other embodiments, the plunger 74 is not set and welded during manufacture, to allow adjustment of plunger 74 after manufacture.

Operation Of Drive Mechanism

In operation, the drive mechanism 20 employs electromagnetic and mechanical forces to move between retracted (FIGS. 3A-D) and forward (FIGS. 4A-D) positions, to cause infusion medium to be drawn into and driven out of the mechanism in a controlled manner. In the retracted position, the spring 68 urges the actuator 36 toward its retracted position shown in FIGS. 3A-D. When the coil 34 is energized to overcome the spring force of spring 68, the actuator 36 moves to its forward stroke position shown in FIGS. 4A-D. The movement of the actuator between retracted and forward positions creates pressure differentials within the internal chambers and volumes of the drive mechanism 20 to draw medium into the inlet 26 and drive medium out the outlet 28.

More specifically, when the coil 34 is de-activated (not energized or not energized in a manner to overcome the spring force of spring 68), the actuator 36 is held in its retracted position (FIGS. 3A-D) under the force of the spring 68. When the coil is de-activated immediately following a forward stroke, the spring 68 moves the actuator 36 to the retracted position of FIGS. 3A-D, from the forward position shown in FIGS. 4A-D.

Figure 12:
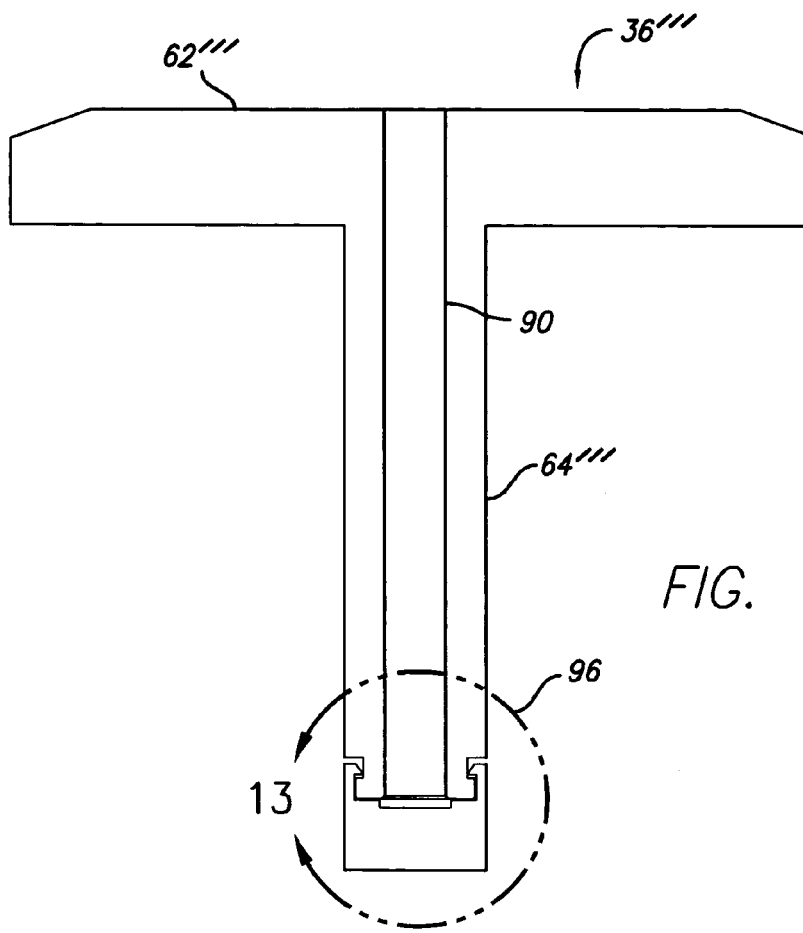
FIG. 12 is a simplified cross-section diagram, showing yet another embodiment of an actuator comprising an armature and a piston for a drive mechanism of the type shown in FIGS. 3A-D and 4A-D and including a valve structure on one end of the piston.

As the actuator 36 retracts, the piston portion 64 of the actuator is retracted relative to the valve member 82, such that a pumping chamber 80 volume is formed or expanded between the end of the piston portion 64 and the valve member 82. The formation or expansion of the pumping chamber 80 volume creates a negative pressure which draws infusion medium from the volume 72 of the cover member 38, through the annular space between the piston portion 64 and the wall of the piston channel 44, and into the pumping chamber 80. While not shown in FIGS. 3A-D, other embodiments (such as shown in FIGS. 10-12) may include one or more channels through the piston portion 64, to provide one or more additional flow paths to the pumping chamber 80.

In the retracted position, a gap is formed between each of the annular inner and outer pole surfaces 54 and 59 on the coil cup member 32 and a respective annular surfaces of the inner and outer pole surfaces 65 and 66 on the armature portion 62 of the actuator member 36. In particular, with reference to FIGS. 3A-D, gaps are formed between the annular pole surfaces of the coil cup member 32 and the armature portion 62 of the actuator member 36.

When the coil 34 is energized (or energized sufficiently to overcome the spring force of spring 68), the actuator member 36 is forced in the direction to close the gaps between the pole surfaces and moves to its forward position (FIGS. 4A-D) under the influence of electromagnetic flux generated by the energized coil. In particular, the coil 34 may be energized by passing an electrical current through the coil conductor to create electromagnetic flux. The electromagnetic flux defines a flux path F as described above with respect to FIG. 9. The electromagnetic flux provides an attraction force between the annular pole surfaces 54 and 59 of the coil cup member 32 and the annular pole surfaces 65 and 66 of the armature portion 62 of the actuator member 36, to draw the armature portion 62 toward the coil cup member 32.

As the armature portion 62 of the actuator member 36 is drawn toward the coil cup member 32, the piston portion 64 of the actuator member 36 is moved axially through the channel 44, in the direction toward the outlet chamber 48. With the coil energized, the piston portion 64 continues to move under the action of the armature, until a mechanical stop is reached, for example, mechanical contact of the armature portion 62 of the actuator 36 with the barrier 61, a portion of the housing member 30 or cover member 38. In other embodiments, the motion may continue until the return force of the spring 68 and fluid pressure inhibits any further forward motion from the electromagnetic force of the energized the coil.

The movement of the piston portion 64 towards the stopping point reduces the volume of the pumping chamber 80 and increases the pressure within the piston chamber until the pressure is sufficient to overcome the force of the valve spring 83. As the valve spring force is overcome by the pressure within the piston chamber, the valve member 82 is moved toward an open position, away from the opening between the pumping chamber 80 outlet chamber 48. When the valve member 82 is in the open position, medium is discharged through the outlet chamber 48 and, eventually, through outlet 28 (FIG. 2). When the coil is deactivated and the piston portion 64 is moved back to its retracted position, the pressure in the pumping chamber 80 reduces and the valve member 82 is reseated under the action of the valve spring 83. This inhibits fluid from flowing back into the drive mechanism, through the outlet. In addition, a negative pressure is created in the pumping chamber 80 to draw medium into the chamber for the next forward stroke, as described above.

In this manner, energization of the coil 34 to move the actuator member 36 from its retracted position (FIGS. 3A-D), to its forward position (FIGS. 4A-D), causes a measured volume of medium to be discharged from the outlet. As described above, when the coil 34 is de-energized, the actuator member 36 is returned to the retracted position (FIGS. 3A-D) under the force of spring 68 and an additional volume of medium is drawn into the pumping chamber 80 for the next discharging operation. Accordingly, the coil 34 may be energized and de-energized by a controlled electronic pulse signal, where each pulse may actuate the drive mechanism 20 to discharge a measured volume of medium. In preferred embodiments, the coil 34 may be electrically coupled to an electronic control circuit (not shown) to receive an electronic pulse signal from the control circuit for example, in response to a sensor signal, timer signal or other control signal input to the control circuit.

In preferred embodiments, when the piston motion is stopped at the end of the forward stroke, the valve-facing end of the piston portion 64 is in close proximity to the valve member 66, for example, spaced from the valve member 82 by no more than about ten percent (10%) of the piston stroke. In further embodiments, the valve facing end of the piston portion 64 is in contact with the valve member 82, at the end of the forward stroke. In this manner, gas that may be present in the infusion medium is less likely to accumulate within the pumping chamber 80. More specifically, in some operational contexts, infusion medium may contain gas in the form of small bubbles that may migrate into the pumping chamber 80 during filling of the piston chamber. As gas is significantly more compressible than liquid, too much gas within the pumping chamber may adversely affect the ability of the drive mechanism to self prime.

In yet another embodiment the piston portion 64 may contact the valve member 82 at the end of the forward stroke and push the valve member 82 open. In this embodiment, it is less likely that gas will be trapped between the piston portion 64 and the valve member 82, and more likely that the chamber will be purged of gas.

Further Drive Mechanism Embodiments

In the embodiments described above, movement of the actuator 36 to the retracted position (FIGS. 3A-D) causes the piston portion 64 of the actuator to retract, such that a pumping chamber 80 volume is formed or expanded between the end of the piston portion 64 and the valve member 82. The formation or expansion of the pumping chamber 80 volume creates a negative pressure which draws infusion medium from the volume 72 of the cover member 38, through the annular space between the piston portion 64 and the wall of the piston channel 44, and into the pumping chamber 80.

The rate at which the infusion medium fills the pumping chamber 80 can depend upon various factors, including the viscosity of the infusion medium and the width of the annular space between the piston portion 64 and the wall of the piston channel 44. To accommodate a greater variety of infusion media and, thus, a greater range of viscosities, embodiments of the invention may employ a piston portion 64 and piston channel 44 configured to improve the flow of an infusion medium into the pumping chamber 80. Such configurations may include one or more of the features described below with respect to FIGS. 10-12.

FIG. 10 shows an embodiment of an actuator member 36' having an armature portion 62' and a piston portion 64', similar in many respects to the armature portion 62 and piston portion 64 of the actuator member 36 described above. However, the actuator member 36' is configured with a central channel 90 extending through the armature portion 62' and the axial length of the piston portion 64'. The channel 90 has openings 92 and 93 on the armature and piston ends of the actuator member 36'. When the actuator member 36' is employed in a pump drive mechanism 20 as shown in FIGS. 3A-D and 4A-D, the channel 90 allows the infusion medium to flow from the cover volume 72, through the piston portion 64' and into the pumping chamber 80. Thus, as the actuator member 36' moves toward a retracted position (the FIGS. 3A-D position of the actuator member), fluidic infusion medium flows through the channel 90 and into the pumping chamber 80.

A valve structure 94 may be provided to control the flow of fluid through the channel 90. For example, a valve structure 94 may be configured to restrict or inhibit a reverse flow of infusion medium from the pumping chamber 80 and back through the channel 90, toward the cover volume 72, during forward strokes of the actuator. In one embodiment, the valve structure may comprise a ball-shaped plug located in a tapered volume, for selectively blocking the flow of infusion medium through the channel 90, as shown in FIG. 10. In other embodiments, other suitable valve configurations may be employed, including, but not limited to a cone-shaped plug in a larger cone-shaped volume, or the like.

The valve structure 94 may be located within the channel 90, for example, adjacent the piston chamber opening 93 of the channel 90. Alternatively, the valve structure 94 may be located in other suitable positions along the length of the channel 90. In further embodiments, the valve structure may include a ball (or other shaped plug) located within the pumping chamber 80, for selectively blocking the opening 93 of the channel 90. In such further embodiments, the opening 93 of the channel 90 may be shaped to cooperate with the shape of the ball (or other shaped plug), to provide a sealing or partial sealing function against back flow of the infusion medium. Thus, for example, the opening 93 may be tapered inward, cone-shaped or the like, to provide a seat for the ball (or other shaped plug) within the pumping chamber 80. In yet further embodiments, multiple valve structures may be located, for example, along the length of the channel 90, at the opening 92, at the opening 93 and/or within the pumping chamber 80, as described above.

During each forward stroke of the actuator member 36', the valve structure 94 closes and the infusion medium is restricted or inhibited from flowing from the pumping chamber 80, through the channel 90, toward the cover volume 72, for example. However, as the actuator member 36' is moved back toward a retracted position, the valve structure 94 opens and allows the infusion medium to flow from the cover volume 72, through the channel 90 and into the pumping chamber 80. In this manner, the channel 90 and valve structure 94 provide a controlled flow path, for the communication of infusion medium into the pumping chamber 80. Moreover, the channel 90 and valve structure 94 may be readily configured with sufficient channel width to allow sufficient filling of the pumping chamber 80 with any one of a variety of infusion media (and, thus, a variety of infusion medium viscosities).

The flow path provided by the channel 90 may be employed in combination with an annular space (described above) between the piston portion 64' and the wall of the piston channel 44, to communicate infusion medium to the pumping chamber 80. In further embodiments, the channel 90 may provide the primary or sole flow path for communication of infusion medium into the pumping chamber 80. In such further embodiments, the annular space between the piston portion 64' and the wall of the piston channel 44 may be minimized.

While embodiments described above employ a single piece actuator member 36', further embodiments of an actuator with a central channel 90 may be employed with multi-piece actuator embodiments, such as the 2-piece actuator member described in U.S. patent application Ser. No. 10/033,722, as the "second drive mechanism embodiment and operation." In such embodiments, the armature portion of the actuator member is separable from the piston portion of the actuator member. For example, the 2-piece actuator member 36" shown in FIG. 11 includes an armature portion 62" and a piston portion 64", configured as two separable pieces.

A channel 90, as described above, is provided through the piston portion 64", but need not be provided through the armature portion 62" of the actuator member 36". A valve structure 94, as described above, may be provided in the piston portion 64". Alternatively, or in addition, a valve structure located in the pumping chamber 80 and/or multiple valve structures as also described above, may be employed with the 2-piece actuator embodiment of FIG. 11.

Figure 13:
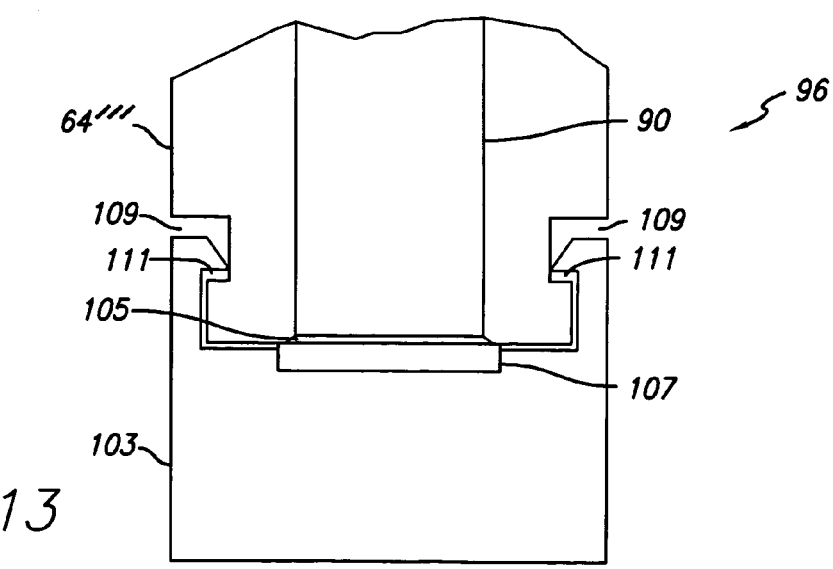
FIG. 13 is a detailed view of an embodiment of a valve structure shown in FIG. 12.

In embodiments as shown in FIGS. 12 and 13, an alternative valve structure may be employed to control a flow of infusion medium from the channel 90 of the piston to the pumping chamber 80. For example, as shown in FIG. 12, actuator member 36''' may include a valve structure 96. Valve structure 96 may be configured to restrict or inhibit a reverse flow of infusion medium from the pumping chamber 80 and back through the channel 90, toward the cover volume 72, during forward strokes of the actuator (FIGS. 4A-D). A more detailed view of one embodiment of valve structure 96 is shown in FIG. 13.

As shown in FIG. 13, one embodiment of the valve structure 96 may comprise a cap 103, a seat 105, and a washer 107. According to embodiments of the present invention, seat 105 has a generally frusto-conical shape. However, any suitable shape may be used, including, but not limited to, flat and radiused. The tapered end of seat 105 is coupled to piston portion 64'''. In one embodiment, seat 105 is integral with piston portion 64'''. Piston portion 64''' may be formed to include indented area 109 for receiving a catch of cap 103. Cap 103 may be placed over the end of piston portion 64''' closest to the piston chamber 80 such that the catch snaps into indented area 109 to secure cap 103 to piston portion 64'''. Cap 103 and seat 105 may be made from any suitable biocompatible material, including, but not limited to, metal and plastic. In one embodiment, cap 103 is made from polysulfone.

Washer 107 is located between cap 103 and seat 105 to provide a sealing function for inhibiting leakage at the interface between seat 105 and washer 107 during forward strokes of the actuator. In this manner, reverse flow of infusion medium is inhibited during forward strokes of the actuator. Cap 103 may include an indentation for seating washer 107. Washer 107 may be press fit into the indentation and/or may be secured within the indentation by means of a suitable adhesive or the like. Washer 107 may be made from any suitable biocompatible material, including, but not limited to, silicone rubber.

During a forward stroke, seat 105 is sealed against washer 107 due to pressure created in pumping chamber 80, and space 111 is formed by the upward movement of the catch within indented area 109. However, during reverse strokes, washer 107 and seat 105 separate from one another due to suction (vacuum) created in pumping chamber 80. Thus, when piston portion 64''' is in a reverse stroke, suction is applied to cap 103 such that cap 103 moves in a direction opposite to the upward movement of piston portion 64'''. Space 111 allows catch to move downward within indented area 109 until the catch comes to a stop against the bottom shoulder of indented area 109. The separation of washer 107 and seat 105 allows flow of infusion medium from cover volume 72 through the channel 90, into pumping chamber 80 during reverse strokes. In one embodiment, space 111 may be equal to approximately 0.002 inches or about 20% of the stroke of piston portion 64'''. Other suitable dimensions may be used in other embodiments of the valve structure 96.

In yet further embodiments, the annular space between the piston portion of the actuator member 36 and the wall of the piston channel 44 may be increased relative to the above-described embodiments, to increase the rate of flow of infusion medium from the cover volume 72, into the pumping chamber 80. For example, as shown in FIG. 12, an actuator member 36''' may be provided with a piston portion 64''' having a reduced diameter relative to the actuator members shown in the above-described embodiments. In such embodiments, the rate at which a given infusion medium may flow through the annular space between the piston portion 36''' and the piston channel 44 is increased (relative to embodiments employing a larger diameter piston portion). Accordingly, the rate of filling of the piston chamber may be increased, for example, to accommodate a greater variety of infusion media.

Alternatively, or in addition to employing an actuator member 36''' having a relatively small diameter piston portion 64''', the diameter of the piston channel 44 may be increased, relative to the above-described embodiments. By employing a relatively small diameter piston portion 64''' and/or a relatively large diameter piston channel 44, the annular space between the piston portion 64''' and the piston channel 44 (and, thus, the rate at which a given infusion medium may flow through the annular space) may be similarly increased.

Various features that may be employed in infusion drive mechanisms for improving operation with a any one of a variety of infusion media are described herein in connection with the embodiment of FIGS. 10-12. Further features that may be employed for improving operation with any one of a variety of infusion media are described herein in connection with FIGS. 3-9. However, it is contemplated that, where possible, features described in connection with one embodiment may be employed in the other embodiment. For example, the armature and coil cup configurations of FIGS. 3-9 may be employed in combination with one or more of the channel 90, valve configurations 94 and increased annular spacing between the piston portion and piston channel described above with respect to FIGS. 10-12. Moreover, embodiments of FIGS. 3-12 may be employed with single-piece actuator configurations or multi-piece actuator configurations.

While drive mechanism embodiments described above employ a coaxial arrangement of the coil, piston channel and piston, other embodiments may employ a piston and piston channel located between, but not coaxial with, a plurality of spaced coils. For example three coils may be located in a spaced relation at three respective corners of a triangle, with the piston channel and piston located in the center of the triangle (surrounded by the three locations of the coils), and with the piston axis parallel to the axes of the coils. In further embodiments more than three coils may be located at discrete positions spaced around the piston (at locations surrounding the piston), preferably, equally spaced from the piston or otherwise arranged to provide approximately equal forces on the piston.

The foregoing description of the preferred embodiment of the invention has been presented for the purposes of illustration and description. It is not intended to be exhaustive or to limit the invention to the precise form disclosed. Many modifications and variations are possible in light of the above teaching.

What is claimed is:

1. A drive mechanism for an infusion device, the drive mechanism comprising:
a first housing having an inlet, the first housing defining an interior volume for receiving fluidic media from the inlet, the interior volume having a width dimension;
a coil arranged to be selectively energized;
an armature moveable in the interior volume of the first housing at least between a retracted position and an advanced position in response to energizing the coil, the armature having a first pair of pole surfaces;
a coil housing containing the coil, the coil housing composed of a magnetizable material and providing a second pair of pole surfaces in a magnetic flux path with the first pair of pole surfaces when the coil is energized;
a second housing containing the coil housing, the second housing defining a piston channel extending through at least a portion of the second housing;
a piston moveable along the piston channel in conjunction with movement of the armature at least between a retracted position and an advanced position to convey fluidic media from the interior volume of the first housing and out the piston channel in a case where the interior volume of the first housing contains fluidic media and the coil is energized to move the armature and the piston to the advanced position, the piston channel having a length dimension along which the piston moves between the retracted position and the advanced position; and
a barrier member arranged between the armature and the coil housing, the barrier member defining an opening through which the piston extends into the piston channel, the opening having a width dimension that is less than the width dimension of the interior volume, the width dimension of the opening and the width dimension of the interior volume transverse the length dimension of the piston channel;
wherein the armature comprises an armature body having a cavity and a magnetic material located within the cavity.

2. The drive mechanism as recited in claim 1, wherein the armature body is composed of a material having a lower magnetic permeability relative to the magnetic material.

3. The drive mechanism as recited in claim 2, wherein the armature body is composed of at least one of titanium, stainless steel, biocompatible plastic, ceramic, and glass.

4. The drive mechanism as recited in claim 2, wherein the armature body is composed of a non-ferritic stainless steel.

5. The drive mechanism as recited in claim 1, wherein the magnetic material comprises at least one of a ferrous material and a ferritic stainless steel material.

6. The drive mechanism as recited in claim 1, further comprising:
a cover provided over the cavity of the armature body to cover the magnetic material located within the cavity.

7. The drive mechanism as recited in claim 6, wherein the cover comprises a foil material.

8. The drive mechanism as recited in claim 1, the armature comprising a cover for inhibiting the magnetic material from contacting fluidic media in the interior volume of the first housing.

9. The drive mechanism as recited in claim 1, wherein the magnetic material located within the cavity completes a flux path when the coil is energized.

10. The drive mechanism as recited in claim 9, the armature comprising a cover for inhibiting the magnetic material from contacting fluidic media in the interior volume of the first housing when the coil is energized.

11. The drive mechanism as recited in claim 10, wherein the cover comprises a foil material.

12. The drive mechanism as recited in claim 1, wherein the first pole surfaces face the same direction.

13. A method for making a drive mechanism for an infusion device, the method comprising:
providing a first housing having an inlet, the first housing defining an interior volume for receiving fluidic media from the inlet, the interior volume having a width dimension;
arranging a coil to be selectively energized;
supporting an armature for movement in the interior volume of the first housing at least between a retracted position and an advanced position in response to energizing the coil, the armature having an armature body and a first pair of pole surfaces;
containing the coil in a coil housing composed of a magnetizable material;
providing a second housing containing the coil housing, the second housing defining a piston channel extending through at least a portion of the second housing supporting a piston in the piston channel for movement in conjunction with movement of the armature in response to energizing the coil to convey fluidic media from the interior volume of the first housing and out the piston channel in a case where the interior volume of the first housing contains fluidic media and the coil is energized to move the armature and the piston to the advanced position, the piston channel having a length dimension along which the piston moves between the retracted position and the advanced position;
arranging the coil housing such that a second pair of pole surfaces on the coil housing are in a magnetic flux path with the first pair of pole surfaces when the coil is energized;
arranging a barrier member between the armature and the coil housing, the barrier member defining an opening through which the piston extends into the piston channel, the opening having a width dimension that is less than the width dimension of the interior volume, the width dimension of the opening and the width dimension of the interior volume transverse the length dimension of the piston channel; and
supporting a magnetic material within a cavity in the armature body for completing the flux path when the coil is energized.

14. The method as recited in claim 13, wherein supporting an armature comprises supporting an armature having an armature body composed of a material having a lower magnetic permeability relative to the magnetic material.

15. The method as recited in claim 13, wherein supporting an armature comprises supporting an armature having an armature body composed of at least one of titanium, stainless steel, biocompatible plastic, ceramic, and glass.

16. The method as recited in claim 13, wherein supporting an armature comprises supporting an armature having an armature body composed of a non-ferritic stainless steel.

17. The method as recited in claim 13, wherein supporting a magnetic material comprises supporting at least one of a ferrous material and ferritic stainless steel material.

18. The method as recited in claim 13, further comprising: covering the magnetic material with a cover provided over the cavity of the armature body.

19. The method as recited in claim 13, further comprising: covering the magnetic material with a foil disposed over the cavity of the armature body.

20. The method as recited in claim 13, further comprising: covering the magnetic material with a cover that inhibits the magnetic material from contacting fluidic media in the interior volume of the first housing.

21. The drive mechanism as recited in claim 13, wherein supporting an armature comprises supporting an armature with the first pole surfaces facing the same direction.

22. The drive mechanism as recited in claim 1, the piston channel extending completely through the coil housing.

23. The drive mechanism as recited in claim 1, the piston having a fluid channel extending through an axial length of the piston, the fluid channel for conveying fluidic media from the interior volume of the first housing.

24. The drive mechanism as recited in claim 23, wherein the fluid channel extends though the armature and the piston.

25. The drive mechanism as recited in claim 1, the magnetic material having a portion extending toward the coil housing such that the portion is closer to the coil housing than a remaining portion of the magnetic material.

26. The drive mechanism as recited in claim 1, wherein the cavity and the magnetic material are annularly shaped.

27. The drive mechanism as recited in claim 1, wherein a portion of the armature extends through the magnetic material.

28. The drive mechanism as recited in claim 1, wherein a portion of the armature is surrounded by the magnetic material.

29. The drive mechanism as recited in claim 1, further comprising:
a bias member arranged in the piston channel to impart a force on the armature toward the retracted position.

30. The drive mechanism as recited in claim 29, the bias member configured to move the piston and armature to the retracted position when the coil is not energized.

31. The drive mechanism as recited in claim 29, wherein the bias member comprises a spring.

32. The drive mechanism as recited in claim 29, the second housing having a ridge portion defining a portion of the piston channel, the ridge portion for supporting the bias member in the piston channel.

33. The drive mechanism as recited in claim 1, the piston arranged such that a side surface extending along an entire length of the piston faces the inner surface of the second housing, the side surface of the piston in contact with the fluidic media being conveyed by the piston from the interior volume of the first housing.

34. The drive mechanism as recited in claim 33, the piston moveable in an axial direction, the axial direction parallel with the side surface of the piston.

35. The drive mechanism as recited in claim 1, wherein the inlet of the first housing is laterally offset from the piston channel.

36. The drive mechanism as recited in claim 35, wherein the inlet of the first housing extends in a direction that is non-parallel with a direction in which the piston channel extends.

37. The drive mechanism as recited in claim 1, wherein the inlet of the first housing is in fluid communication with the interior volume of the first housing in a case where the armature and the piston are in the retracted position.

38. The drive mechanism as recited in claim 1, wherein the inlet of the first housing is in fluid communication with the piston channel in a case where the armature and the piston are in the retracted position.

39. The drive mechanism as recited in claim 1,
wherein the coil housing has a width dimension that is transverse the length dimension of the piston channel; and
wherein the width dimension of the interior volume is at least as great as the width dimension of the coil housing.

40. The drive mechanism as recited in claim 1, wherein the opening of the barrier member has a length dimension that is less than the width dimension of the opening of the barrier member.

41. The drive mechanism as recited in claim 1,
wherein the coil housing has a width dimension that is transverse the length dimension of the piston channel;
wherein the first pair of pole surface has a width dimension that is transverse the length dimension of the piston channel;
wherein the barrier member has a width dimension that is transverse the length dimension of the piston channel and is at least as great as the width dimension of the coil housing and the width dimension of the first pair of pole surfaces of the armature; and
wherein the barrier member has a thickness that is less than the width dimension of the barrier member.

42. The drive mechanism as recited in claim 1, wherein the armature has a width dimension that is transverse the length dimension of the piston channel and is greater than the width dimension of the opening of the barrier member.

* * * * *